US012802793B2

(12) United States Patent
Han

(10) Patent No.: US 12,802,793 B2
(45) Date of Patent: Nov. 17, 2026

(54) AI-DRIVEN HEALTHCARE INFORMATION MANAGEMENT SYSTEM

(71) Applicant: Mo Han, Buffalo, NY (US)

(72) Inventor: Mo Han, Buffalo, NY (US)

(73) Assignee: Mo Han, Buffalo, NY (US)

( * ) Notice: Subject to any disclaimer, the term of this patent is extended or adjusted under 35 U.S.C. 154(b) by 0 days.

(21) Appl. No.: 19/060,097

(22) Filed: Feb. 21, 2025

(65) Prior Publication Data

US 2026/0253684 A1 Aug. 27, 2026

(51) Int. Cl.
*G16H 10/60* (2018.01)
*G06F 40/205* (2020.01)

(52) U.S. Cl.
CPC ........... *G16H 10/60* (2018.01); *G06F 40/205* (2020.01)

(58) Field of Classification Search
CPC .............................. G16H 10/60; G06F 40/205
See application file for complete search history.

(56) References Cited

U.S. PATENT DOCUMENTS

| | | | | |
|---|---|---|---|---|
| 12,222,898 | B1 * | 2/2025 | Madan | G06F 16/144 |
| 2024/0029848 | A1 * | 1/2024 | Gupta | G16H 15/00 |
| 2024/0160953 | A1 * | 5/2024 | Manda | G06F 16/5846 |
| 2024/0312233 | A1 * | 9/2024 | Kumar | G06V 30/18 |
| 2024/0412720 | A1 * | 12/2024 | Vasylyev | G06F 40/35 |
| 2025/0045256 | A1 * | 2/2025 | Gottlob | G06F 16/211 |
| 2025/0046409 | A1 * | 2/2025 | Thompson, IV | G16H 70/60 |
| 2025/0068668 | A1 * | 2/2025 | Grbic | G16H 30/40 |
| 2025/0111204 | A1 * | 4/2025 | Eggert | G06F 16/3347 |
| 2025/0131997 | A1 * | 4/2025 | Forester | G16H 10/20 |
| 2025/0156634 | A1 * | 5/2025 | Klafter | G06F 16/953 |

* cited by examiner

*Primary Examiner* — Fonya M Long
*Assistant Examiner* — Anthony Balaj
(74) *Attorney, Agent, or Firm* — Reising Ethington P.C.

(57) ABSTRACT

A healthcare information management system includes an interface layer, a processing layer, and a database layer. Patient healthcare information received in the processing layer from the interface layer is processed to extract relevant data for population of a structured database of the database layer. The received information can include unstructured information. The processing layer is equipped to use one or more AI models to facilitate data extraction, understand user requests, and retrieve pertinent data from the structured database to generate outcomes in response to those requests. The system is able to receive information in multiple different formats, including structured and unstructured formats, and process the information to transform relevant data extracted from the received information into one structured database with a unified schema. Information can be received from multiple user interfaces at multiple locations, and the structured data can be accessed similarly.

18 Claims, 12 Drawing Sheets

| | Patient ID | Heart Rate | Total Cholesterol | ... | *Health Indicator* |
|---|---|---|---|---|---|
| Time Point 1 | John Doe | 78 | 168 | | |
| Time Point 2 | John Doe | 81 | 172 | | |
| Time Point 3 | Jane Doe | 83 | 159 | | |
| ... | | | | | |
| Time Point n | | | | | |

*FIG. 2*

| Field Name | Heart Rate | Total Cholesterol |
|---|---|---|
| Instruction | What is the patient's heart rate at rest? If you do not know, then return NA. | What is the patient's total cholesterol level? If you do not know, then return NA. |
| Value Format | Integer number | Integer number |
| Units | Beats per minute (BPM) | Milligrams per deciliter (mg/dL) |
| Possible Values | 30-220 | 0-500 |
| Example Value | 72 BPM | 155 mg/dL |
| ... | | |
| *Parameter* | | |

*FIG. 3*

AI-DRIVEN HEALTHCARE INFORMATION MANAGEMENT SYSTEM

TECHNICAL FIELD

The present disclosure is related generally to healthcare information management and, more particularly, to computer-implemented systems and methods for improving management and use of healthcare information.

BACKGROUND

In the modern age, patient healthcare data is typically stored electronically, which has advantages over physical records-based storage, such as the ability to access the data from different remote locations, to electronically search the data, and to greatly reduce physical space requirements. However, as patient healthcare data has transitioned to electronic storage, other problems have arisen that have kept the usefulness of electronic records far from their full potential. One significant problem is the general fragmentation of each patient's healthcare data across multiple data management systems operated by different entities and stored in different formats. This fragmentation makes critical health information inaccessible in real-time, which can hinder timely interventions. Manual data extraction is inefficient and error-prone due to inconsistent and unstructured formats. For example, patient data stored in one electronic medical records (EMR) system cannot be accessed by another EMR system because the two different EMR software providers store the data in different and often proprietary formats, platforms, or systems. Moreover, a significant portion of patient healthcare data may exist in a format with no structure at all or exist at multiple distinct locations, making it difficult to find and perhaps wasting its potential usefulness to patients and providers alike.

SUMMARY

Embodiments of a healthcare information management system include a structured database and a data processor. The structured database stores healthcare data of one or more patients in non-transient memory according to a unified schema having a plurality of distinct data fields, each data field being pre-defined by a plurality of distinct parameters. The data processor receives from at least one user interface healthcare information of each patient and is configured to use artificial intelligence to extract relevant data from the received healthcare information for storage in the structured database or to retrieve pertinent data from the structured database in response to an outcome request. Relevant data is defined as data for which there is a pre-defined data field in the structured database, and pertinent data is defined as data in the structured database that is pertinent to the outcome request.

In various implementations, the received healthcare information includes unstructured information, and the data processor is configured to use artificial intelligence in an information ingestion process that includes interpreting and processing unstructured portions of the received information and extracting relevant data from the interpreted and processed data.

In various implementations, the data processor is configured to extract relevant data from a data dump comprising the received healthcare information using a large language model (LLM) by providing to the LLM a pre-defined LLM data extraction instruction, definitions of each data field, and relevant portions of the data dump to search for the relevant data.

In various implementations, the data processor is configured to identify relevant portions of the data dump and extract relevant data from the relevant portions using a retrieval-augmented generation (RAG) method.

In various implementations, the data processor is configured to: generate a single data dump representing the received healthcare information, identify relevant portions of the data dump to search for relevant data, search the relevant portions of the data dump to extract relevant data using a large language model (LLM) and a pre-defined LLM data extraction instruction, and store the extracted data in the pre-defined data fields of the structured database.

In various implementations, the data processor is configured to simultaneously receive the healthcare information in at least two different file formats, understand and parse the received information, and generate a single data dump from the understood and parsed information.

In various implementations, the data processor is configured to generate vector embeddings representing at least some of the received information and include the vector embeddings in a single data dump.

In various implementations, the data processor is configured to convert unstructured portions of the received healthcare information to text, chunk the text, generate vector embeddings based on the chunked text, and include the vector embeddings in a single data dump.

In various implementations, the data processor is configured to use a large language model (LLM) and a pre-defined LLM graph generation instruction to generate a graph from chunked text and generate vector embeddings from the graph.

In various implementations, the data processor is configured to identify relevant portions of a data dump and extract relevant data from the relevant portions using a graph-based retrieval augmented generation (GraphRAG) method.

In various implementations, the data processor, in response to receiving the outcome request, is configured to use one or more large language models (LLMs) to understand the request and retrieve the pertinent data from the structured database, the requested outcome being generated based at least in part on the retrieved pertinent data.

In various implementations, the data processor is configured to use the structured database as an input to an LLM to understand the outcome request and retrieve the pertinent data.

In various implementations, the data processor is configured to generate processed pertinent data by providing to an LLM a pre-defined LLM instruction, retrieved pertinent data, and details of the outcome request. The processed pertinent data includes at least one of: a summary of the pertinent data, an analysis of the pertinent data, or insights based on the pertinent data.

In various implementations, the data processor is configured to generate a formatted output by providing to an LLM a pre-defined LLM outcome generation instruction, retrieved pertinent data, processed pertinent data, details of the outcome request, and a specified output format.

In various implementations, the pertinent data includes data extracted from received healthcare information previously input into the system in multiple different file formats.

In various implementations, the data processor is configured to use one or more large language models (LLMs) to identify potential new data fields to add to the structured database, inputs to the LLM being based at least in part on:

an LLM data extraction instruction, a data dump generated by the data processor prior to extraction of the relevant data from the received healthcare information, and definitions of each data field of the structured database. The data processor stores identified potential new data fields in a pool of potential new data fields and is configured to add one or suggest adding one or more fields of the potential new data fields in the pool to the structured database when said one or more fields of the potential new data fields reaches a threshold significance.

In various implementations, the system includes a data field customization interface by which a user can add new data fields, remove existing data fields, or modify existing data fields of the structured database.

In various implementations, the database includes one or more data fields or metadata identifying one or more entities authorized to access at least one data field of the structured database. The data processor, in response to receiving the outcome request from a user, is configured to determine whether the user has authority to access the at least one data field before generating the outcome.

It is intended that any one or more of the above-listed features, along with any of the features in the figures and in the following description, can be combined in any technically feasible combination to define a claimed invention, except where features are mutually exclusive.

BRIEF DESCRIPTION OF THE DRAWINGS

Illustrative embodiments will hereinafter be described in conjunction with the following figures, wherein like numerals denote like elements, and wherein:

FIG. 2 depicts an example of a structured database including patient healthcare data;

FIG. 3 depicts examples of parameters defining data fields of the structured database;

DESCRIPTION OF ILLUSTRATIVE EMBODIMENTS

Figure 1:
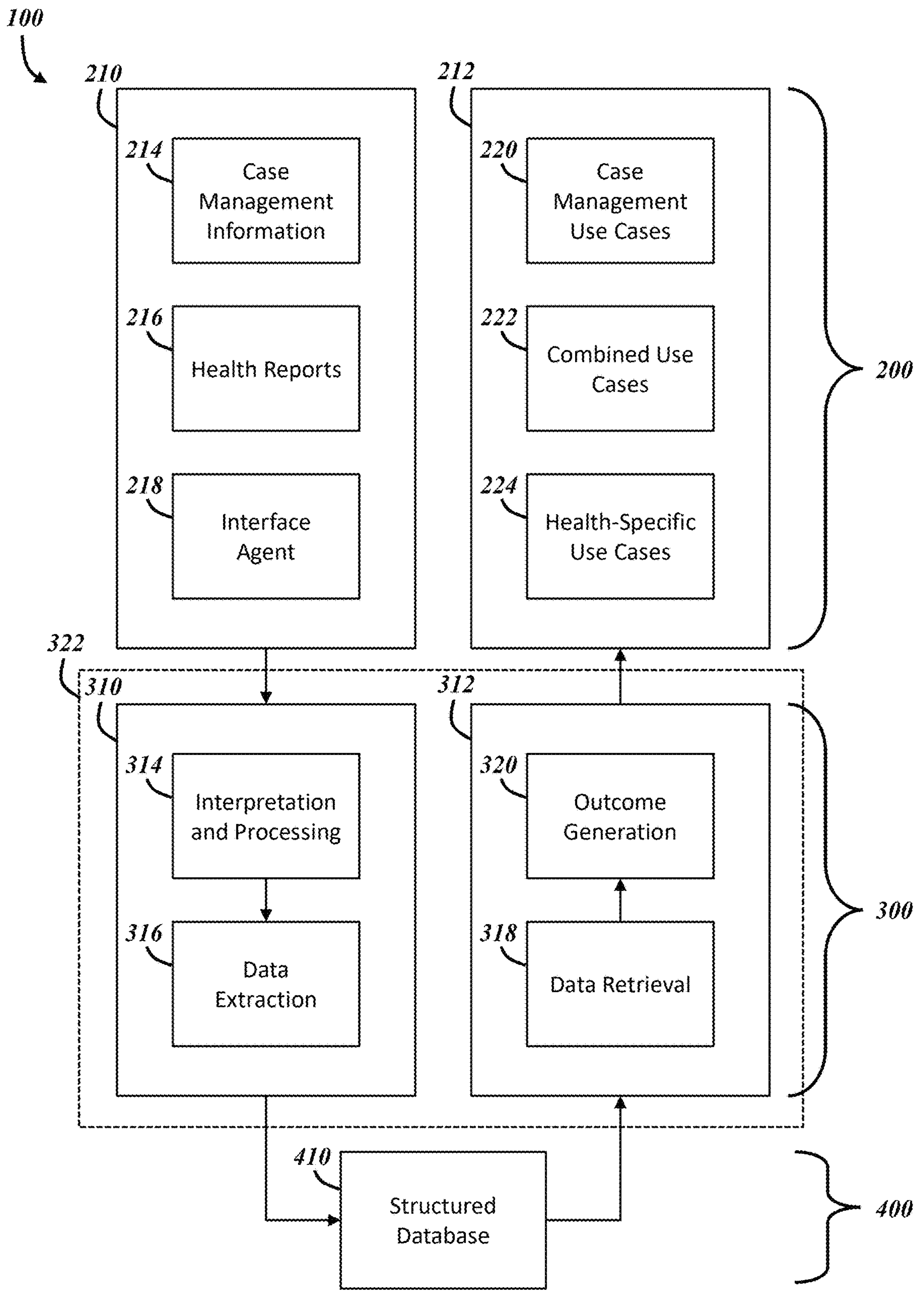
FIG. 1 depicts an embodiment of a healthcare information management system.

Described below is a healthcare information management system and related methods of managing patient healthcare information, including formation and use of a structured database built from information that includes unstructured information. The system and methods leverage artificial-intelligence (AI) data processing to decipher information originating in multiple different formats or from multiple different sources for entry into the structured database, thus providing one centralized database with patient data in a unified schema from which users, or the system itself, can retrieve information to suggest or make decisions about a patient's healthcare.

The following are definitions of certain terms used in this disclosure.

"Information" has its ordinary and customary meaning, which is knowledge of any form, whether expressed in a tangible medium, displayed, broadcast, or retained in human memory.

"Data" is information in digital or computer-readable form. Data usually includes some relationship among distinct pieces of information. For example, a person's birthdate as a piece of data is typically associated with the person.

"Structured," as used with "information" or "data," means that the information is organized according to a defined schema.

"Unstructured," as used with "information" or "data," means that at least a portion of the information is not organized according to a defined schema.

"Healthcare" is care provided to a patient that seeks to maintain or improve the patient's physical or mental health or seeks to improve quality of life for a patient with a physical or mental impairment.

"Healthcare information" is information that may be required or used by a healthcare provider to render healthcare to a patient.

"Healthcare data" is healthcare information in digital or computer-readable form.

"Relevant data" is data for which the structured database has a defined data field.

"Relevant information" includes relevant data along with other information from which relevant data can be extracted.

"Artificial intelligence" (abbreviated as "AI") is any of a set of computer-implemented techniques, including machine learning, that is designed to approximate a cognitive task. Such techniques may be embodied as one or more AI models.

An "AI model" is a computer-executed program that applies one or more algorithms to data to recognize patterns, make predictions, or make decisions without human intervention.

A "user" of the disclosed system and methods is a human who interacts with the system via a user interface. Users may be categorized as patients or providers.

A "patient" is a receiver of healthcare and, for purposes of this disclosure, is any person whose healthcare information is stored as structured data by the system.

A "provider" is a healthcare provider who provides healthcare to a patient, a service provider (e.g., an insurance company) who provides a healthcare-related service to a patient, or an agent of a healthcare or service provider. Providers may include organizations, such as government-sponsored insurance providers or other government agencies or organizations having a use for information stored by the disclosed system.

Some of the terms defined above are further elaborated upon in the discussion below.

FIG. 1 schematically illustrates an embodiment of an AI-driven healthcare information management system 100. While described below in conjunction with several specific use cases, the system 100 is applicable to any healthcare setting, including but not limited to home care, nursing homes, hospitals, long-term care, day care, etc. The system 100 is a multi-layer computer-implemented system structured as and including an interface layer 200, a processing layer 300, and a database layer 400. The three layers 200-400 and their respective components are or can be interconnected and in communication with each other via one or more computer networks, such as, without limitation, the internet, local area networks (LANs), Wide Area Networks (WANs), Virtual Private Networks (VPNs), peer-to-peer connections, and/or cellular networks. The system 100 could also be embodied as a single computer.

The interface layer 200 is structured with an input side 210, configured to collect information for processing by the system 100, and an output side 212, configured to present information retrieved from the system. Embodiments of the system and methods of using the system include collecting information from human users and presenting retrieved information to human users. The processing layer 300 has an incoming side 310 that receives patient healthcare information from the interface layer 200 and processes that information to identify patient healthcare data for storage in a structured database 410 of the database layer 400. At least some of the received patient healthcare information may be unstructured information. The processing layer 300 also has an outgoing side 312 configured to retrieve patient healthcare data from the structured database 410 and process the data for presentation at the output side 212 of the interface layer 200. The processing layer 300 uses artificial intelligence (AI) to process information received from the interface layer 200 and/or to process data retrieved from the structured database 410 to generate outcomes for presentation at the interface layer.

Any process, method, or process or method step described herein may be computer-implemented, meaning that it is performed by a computer processor of a computer equipped with non-transient memory storing computer code that, when executed by the processor, cause the computer to perform the method or method steps. Generally, in the illustrated system 100, tasks performed in the processing layer 300 are computer-implemented, while tasks in the interface layer 200 may be partly computer-implemented and usually involve a human user performing certain tasks and/or receiving information from the system.

As noted above, information and data can be structured or unstructured. The patient healthcare data stored in the structured database 410 is structured data. Structured data is easily searchable and readily consumable for downstream applications such as analytics tools, reporting systems, and AI pipelines. The well-defined schema simplifies automation, enhances data quality, and supports scalable processing. Conversion of and extraction of relevant data from received information from different sources and in different formats to a standardized format—i.e., the schema of the structured database 410—allows the stored data to be easily shared in the same structure across different parties, thus enabling caregivers to extract insights quickly, automate workflows, and make accurate data-driven decisions.

The schema according to which the data is organized in the structured database 410 is pre-defined, meaning that the schema is determined before the data is stored there. The schema may have a plurality of pre-defined distinct data fields, and each data field may be pre-defined by a plurality of distinct parameters. The system 100 may be configured to use the schema not only as an organizational structure for the patient healthcare data, but also as an aid in processing incoming information to identify data for placement in the appropriate data fields of the schema. The schema may be or may include an array of rows and columns such as a table. For example, the structured database 410 may be a relational database that is searchable using structured query languages (e.g., SQL). The schema of the structured database 410 may be a unified schema, meaning that the schema is the same for each patient whose healthcare data is stored in the database. As used herein the terms "row" and "column" as used to describe features of an array are arbitrary. In other words, rows may be horizontal or vertical such that the columns of the same array are vertical or horizontal, respectively.

A portion of a non-limiting example of a structured database 410 is schematically illustrated in FIG. 2 as an array 412 of patient healthcare data. The illustrated array 412 is a table containing patient healthcare data 414 for more than one patient. In this example, each row (extending left-right in FIG. 2) represents a discrete time point associated with the data in that row, and each column (extending up-down in FIG. 2) represents a pre-defined data field 414*a*, 414*b*, 414*c* . . . 414*x*. Each data field 414*a-x* is associated and/or populated with a discrete piece of patient healthcare data. In this example, each data field 414*a-x* for which there is a time point is populated with a discrete piece of patient healthcare data. In other examples, only one data field per row and per patient is populated. The array 412 is not limited to time points defining each row. Each row may represent some other variable within the data, such as patient ID, location, or data source. Each discrete piece of data populating one of the data fields 414*a-x* may be referred to as a "value," which can be either a numerical value or a text string. One or more of the data fields 414*a-x* may be defined such that the value in that field is qualitative and may contain words or sentences. Some of the data fields may be defined with binary values such that the data field is populated a "Y" or "N" or equivalent. Other data fields may be defined to contain values selected from a pre-defined list of values.

In the illustrated example, one of the data fields 414*a* is defined to contain a patient ID (e.g., name or assigned number) representing the patient that the data in that row is pertinent to. In other examples, the structured database 410 is a 3D array with an identical 2D array of data fields 414*a-x* for each distinct patient. A different third dimension of such an array schema could be based on a variable other than patient ID. A 3D array may for example include a 2D array as in FIG. 2 with an identically structured array containing metadata for each data field 414*a-x*. In other examples, each data field 414*a-x* includes a metadata parameter. An example of metadata for a given data field may be "Permissions," where the parameter includes names, ID numbers, or categories of users who are permitted to access or use the data in the respective data field. Similarly, the schema may include metadata as one of the pre-defined data fields 414*a*-*x*. Other examples of metadata include the source of data, identification of user uploading the data source, location, etc.

FIG. 3 schematically illustrates an example of definitions 416 for each data field 414*a*-*x* of the structured database 410. Each data field 414*a*-*x* may be defined by a plurality of distinct parameters 418 as shown in the example of FIG. 3, which illustrates data field definitions 416*b* and 416*c* for data fields 414*b* and 414*c* of FIG. 2. In this example, the list of parameters 416 defining each data field 414*b*-*c* includes a Field Name 418*a*, an Instruction 418*b*, a Value Format 418 *c*, Units 418 *d*, Possible Values 418 *e*, and an Example Value 418*f*. Other parameters 418 *x* may be defined for each data field 414*a*-*x*, and different data field categories (described further, below) may use different parameters than data fields of other categories. In some embodiments, all data fields are defined by a unified set of parameters 418*a*-*x*, meaning that the same list of parameters is used to define each data field. Other examples of the Value Format parameter 418*c* include text, floating point number with a specified number of decimal places, or a list of words. For a data field named "Allergens," for example, the Value Format 418*c* may be "list of words" with no units 418*d* and with the Example Value parameter 418*f* being "pollen, nuts." In some cases, the Possible Values parameter 418*e* is limited to a finite list of options, such as "yes, no," when the data field indicates an answer to a yes/no question, or "0, 1, 2, 3, 4, 5" when the data field indicates an answer such as a rating or level of progression. Unique to the illustrated data field parameters 418*a*-*x* is an Instruction parameter 418*b*. While the other parameters listed in FIG. 3 may be viewed as placing limitations on the data eligible to populate the associated data field, the instruction parameter 418*b* can be used by an AI model in the processing layer 300 to help identify relevant data to extract from the incoming information.

While not shown explicitly, embodiments of a method of using the system may include a step of defining the data fields 414*a*-*x* as discussed above, which happens prior to information ingestion by the system 100. Defining the data fields can reoccur later, even after the database 410 is populated with data, in a process of adding, deleting, or modifying the data fields 414*a*-*x* of the database schema or modifying the data field definitions 416 or parameters 418.

The data fields 414*a*-*x* and/or incoming information may be further designated as belonging to one of a plurality of categories of information. A non-limiting list of categories includes personal information, general information, tests and check-ups information, hospitalization information, physical information, activities of daily living (ADL) information, instrumental ADL (iADL) information, mental health information, and other information.

Examples of personal information include, but are not limited to, a patient's name, address, Medicaid ID, date of birth (DOB), gender, phone number, contact person information, Medicaid eligibility, or whether the patient is capable to direct their own care. Some personal information may be used as index information in the database layer.

Examples of general information include, but are not limited to, information pertinent to the general state of the patient's body, such as age, weight, height, smoking history, alcohol consumption, allergies, diagnoses, medical history, medication use, health stability, medical stability, recent surgeries, sleep wellness, or dietary information.

Examples of tests and check-ups information may include, but are not limited to, blood sugar level, total cholesterol level, heart rate, respiratory rate, number of check-ups annually, last check-up date, number of dental check-ups annually, date of last dental cleaning, eye and ear check-up information, or sexual health information.

Examples of hospitalization information may include, but are not limited to, number of ER visits in past year, reasons for ER visits, number of hospitalizations in past years, duration of last hospital stay, or reason for last hospitalization.

Examples of physical information may include, but are not limited to, incident reports including severity and outcome, cognitive or decision-making impairment levels, short-term or long-term or procedural memory loss level, hearing or visual difficulty levels, locomotion mode, bladder or bowel incontinence, wandering tendencies, independent transfers, wound or skin issues, catheter or ostomy or feeding tube information, incontinence supply or durable medical equipment (DME) order information, recent fall information, recent acute care or skill nursing facility (SNF) admissions, physical activity or pain or mobility impairment levels, sleep quality, medication adherence, behavioral concerns, rehabilitation therapies, flu and other vaccine information, exercise information physical activity engagement level, screening test information, chronic illness information, or physical disability information.

Examples of ADL information may include, but are not limited to, whether the patient can independently manage: personal hygiene, dress their upper or lower body, walking or other ADLs; whether the patient needs assistance with ADLs; whether the patient has good hygiene practices and the level of those practices; number of daily hand-washings; dietary habits; or how balanced their diet is.

Examples of iADL information may include, but are not limited to, whether the patient can independently: prepare their meals, do their laundry and housekeep, manage their finances, use the phone, navigate stairs, shop, manage their transportation, bathe, or perform other iADLs; whether the patient: is in a nursing home or at risk of requiring nursing home care, has a stable living environment, is a candidate for home care services, participates in person-centered planning, has access to healthcare services, or has completed a home evaluation; living arrangements; health-based lifestyle changes; recent health service usage; or financial impact of the patient's health.

Examples of mental health information may include, but are not limited to, negative mental health status level, social interaction level, social support system information, emotional wellness level, whether the patient has regular mental health check-ups, or how the patient manages mental health issues.

Examples of other information may include, but are not limited to, care or treatment concerns expressed by the patient, the patient's level of health literacy, the patient's level of satisfaction with healthcare services, or other information that does not fit neatly into another category.

These categories and examples of information in each category are merely illustrative and may be tailored to the particular system and the manner in which and environment in which it is employed. The structured database 410 may include a data field populated with or available for population by a discrete piece of patient healthcare data falling into a pre-defined category and pre-defined health indicator as discussed further below.

As noted above, unstructured information or data includes information that is not organized according to a defined schema. The disclosed system 100 is configured to process unstructured incoming information and identify relevant data for storage in the structured database. "Relevant data" is data for which there is a data field 414*a-x* defined within the schema of the structured database 410. An example of unstructured information for a given collection of information is information that is provided in more than one computer file format, such as portable document format (PDF), DOCX format, text format, audio format (e.g., MP3, WAV, etc.), image format (e.g., JPG, GIF, PNG, etc.), video format (MPG, MP4, etc.), or a proprietary or open-source format of a commercial electronic medical records (EMR) system (e.g., Epic®, Athena®, Praxis®, etc.). Here, "file format" is given its ordinary and customary meaning, which is a standard way information is encoded for storage in a computer file, such that the same written document saved in PDF format and DOCX format are considered to have different file formats. Similarly, the same image stored in JPG and PNG formats are considered to have different file formats even though they are both image formats.

Many commonplace computer file formats are considered to be made up of unstructured data for purposes of this disclosure, even when the incoming information contains only one type of computer file format. For example, while a PDF file containing a scanned document of a patient's diagnosis may have its own defined structure by which the file is saved and opened, that file contains only unstructured healthcare information. This is because the diagnosis information is part of a digital image and can only be discerned by a person opening the file and viewing it. Even if the PDF file is text-searchable, the diagnosis is still unstructured information by virtue of the fact that a search is required to find the information—i.e., the diagnosis information is not stored in the PDF file according to any defined schema by which the information can be identified by a user or computer. In general, image files, audio files, and video files from which relevant patient healthcare data can be extracted contain only unstructured healthcare information. Many text-based computer file formats also contain only unstructured information. For example, a text chat log or email chain might have relevant healthcare information, but not in any defined schema by which that information can be reliably identified.

In some cases, information received by the system 100 from the interface layer 200 may be or may include structured data. A spreadsheet file saved in comma-delimited text format, for example, may include relevant healthcare information or data in a defined schema (e.g., a table). The same may be said about an EMR database file. The disclosed system 100 is also configured to process such structured information to identify relevant data and transform is to the schema of the structured database. For example, incoming structured data might include some of the same data fields 414*a*-414*x* as the structured database 410 but less than all of the data fields, extra data fields, and/or data fields with the same field name or type (e.g., heart rate) but defined differently (e.g., different units). The system 100 is configured to extract relevant data from the incoming structured data and transform it to the degree necessary to be stored according to the schema of the structured database 410. It is also important to note that the system 100 can receive pre-structured healthcare information or data organized according to the schema of the structured database for direct population of the corresponding data fields. For example, a patient may complete a survey with information tailored to be directly entered into the structured database, effectively bypassing the incoming side of the processing layer 300. Or a provider may already have relevant data for the structured database 410 and may enter it directly. Also, the processing layer 300 and database layer 400 may operate independently such that the system 100 can process incoming information to identify and extract data according to the defined data fields of the database 410. The extracted data can then be uploaded directly to the database 410.

In some implementations, the structured database 410 can be contributed to and/or accessed by multiple different users, including multiple healthcare providers, institutions (e.g., hospital systems), organizations (e.g., insurance companies), and/or patients whose data is contained in the database. The system 100 and database 410 could for example be managed by a third-party service provider who solicits contributions to the database from any category of user and provides access to the database 410 to subscribers. In an exemplary implementation, the database 410 is a centralized database containing healthcare data for all patients of a nation or other region and can be contributed to and/or accessed by any category of user with appropriate access control to comply with applicable laws or regulations (e.g., HIPAA). The system 100 is thus capable of centralizing healthcare data in a manner permitting any healthcare provider to instantly access data for a particular patient based on information originating from any number of different providers at different locations who have ever provided care to that patient, regardless of that information's original format or who contributed the information to the database. The system 100 could of course be smaller in scale as well, with each provider or network of providers maintaining their own structured database, which would still provide benefits of its own. One provider, for example, could selectively provide access to their structured database to other providers, and the structured format would make it easy for others to search for and find useful data or process the data to generate their own outcomes.

Referring again to FIG. 1, the interface layer 200 is configured to receive information from and present information to human users via a user interface, such as a computer or computer terminal equipped with a human-machine interface (HMI), such as a keyboard, microphone, or touchscreen, by which a user can provide information to the system 100 and/or a display, speaker, or printer, by which the system can present information to a user. Other examples of user interfaces include but are not limited to telephones, cameras, text messaging interfaces, etc. A computer of the interface layer may include a processor and memory from which the processor executes software code facilitating the transfer of information and data via the user interface. Such a computer may be a desktop or laptop computer or a mobile electronic device (e.g., a smart phone or tablet) running a software app or accessing a webpage, web app or server providing user access to the system 100 via a user portal, for example. For purposes of this disclosure, mobile electronic devices such as tablets and smartphones are considered computers. The interface layer 200 is a dynamic layer in that the number of user interfaces (e.g., computer access points) may continuously change as individual computers or computer systems connect and disconnect from the remainder of the system 100. In some cases, the system 100 may include only the processing layer 300 and the database layer 400 and their respective components, with one or both layers 300, 400 configured for intermittent and/or selective communicative connection with a plurality of different user interfaces equipped to interact with human users.

Patient healthcare information flows into the system 100 at the input side 210 of the interface layer 200, and patient healthcare information, based at least in part on patient healthcare data from the database layer 400, flows out of the system at the output side 212 of the interface layer. It should be understood that the input and output sides 210, 212 of the interface layer 200 are not strictly limited to one-way communication. For instance, at the input side 210, the system 100 may be configured to prompt a user for information. Likewise, a user may enter a request for information into the system at the output side 212. In other words, "input side" and "output side" are in reference to whether patient healthcare information is flowing respectively toward or away from the database layer 400. A user interface may be a single computer in the interface layer 200 representing one endpoint of both the input side 210 and output side 212 of the interface layer.

FIG. 1 illustrates some illustrative categories of sources of patient healthcare information at the input side 210 of the interface layer 200, including case management information 214, health reports 216, and an interface agent 218. Case management information 214 may include knowledge from a healthcare provider, such as documents, user-typed text, and EMRs. Health reports 216 may include lab or test results from multiple different parties (e.g., MRI and report from a radiologist, third-party bloodwork results, etc.). The interface agent 218 may be an AI chatbot, human text or video chat agent, or a human or AI-based voice agent that collects information from patients or providers by prompting the user with questions to be answered with the information. Or the interface agent 218 may provide a file uploader or general instruction on how to input information into the system. The incoming information may include multiple sources of information in the same category or the same source of information at a different time points. For example, incoming information may include multiple health reports 216 from different institutions or from the same institution but at different time points—i.e., even if there are multiple health reports, each health report is a distinct source of information.

FIG. 1 also illustrates examples of use cases—i.e., manners in which users can use or derive benefit from the structured database 410 and/or AI-processing of data from the database layer 400. The illustrated examples include case management use cases 220, combined use cases 222, and health-specific uses cases 224. Case management use cases 220 may involve a healthcare provider accessing or automatically receiving patient healthcare information from the processing layer 300 or directly from the database layer 400 to help the provider make informed decisions about a patients care or treatment. Case management use cases 220 may include case manager training or daily task arrangements. One example of combined uses case 222 is a question and answer session between a provider and the system 100. The interface layer 200 may for example be configured to receive a question or search query from a provider via a user interface and to return a result from the outgoing side 312 of the processing layer 300 based on data from the database layer 400. This type of interaction may be facilitated by a chatbot or a human or AI-based voice agent operating in the interface layer 200, for example. Examples of health-specific use cases 224 include a health-indicator monitor for a particular patient, pre-diagnoses for patients when particular health-related trends are noticed by the system, plan-of-care (POC) and assessment generation, or health-risk detection. More specific examples of use cases are discussed further below.

As shown in the example of FIG. 1, the incoming side 310 of the processing layer 300 is configured to receive patient healthcare information from the interface layer 200 and process the received information to identify relevant data for storage in the structured database 410. In this example, the processing includes an interpretation and processing step 314 and a data extraction step 316. In the interpretation and processing step 314, incoming information, which may include unstructured information, is parsed to understand what types and categories of information are contained in the incoming information and processed for ease of data extraction. This process 314 may employ one or more AI models, some of which are discussed further below. In some cases, the interpretation and processing step does not employ an AI model. In one example, the received information is in the form of a PDF file and the interpretation and processing step 314 involves only data cleaning and chunking. As discussed further below, the chunking process may employ AI or may employ simple segmenting text by token size per chunk. Once the content of the incoming information has been parsed and understood, relevant data is extracted for entry into the structured database 410 in the data extraction step 316. The data extraction step 316 may employ one or more AI models, as discussed further below.

The outgoing side 312 of the processing layer 300 is configured to transform patient healthcare information from the database layer 400, such as patient healthcare data from the structured database 410, to a generated outcome via a data retrieval step 318 and an outcome generation step 320. In the data retrieval step 318, patient healthcare data pertinent to the outcome to be generated is retrieved from the structured database 410. The location of the pertinent data in the database 410 is known by virtue of the defined schema of the database. In other words, retrieving the pertinent data does not require a new search through information of various formats, from various sources or institutions, or from various different time points. The outcome generation step 320 includes using the retrieved data to generate a user-requested outcome or an auto-generated outcome. Specific examples are described below. Depending on the specific use case, the outcome generation step 320 may also employ one or more AI model, some of which are discussed further below. Some use cases may not require an AI model for outcome generation.

The processing layer 300 may be embodied as a data processor 322. As used herein, a "data processor" is more than a computer processor. The data processor 322 is a computer or server equipped with a processor configured to execute computer code stored in non-transient memory to perform the steps such as those illustrated in the processing layer 300 and others discussed herein. At least a portion of the computer code executed by the processor of the data processor 322 may be in the form of an AI model. The data processor 322 thus may further include, in addition to a conventional computer processor, an AI accelerator or machine learning processor suitable for execution of AI models and for processing information and data using AI models. The data processor 322 may for example be a computer server configured to receive patient health information from the interface layer 200, process the received information using one or more AI models, and extract and store the resulting patient healthcare data in the structured database 410. While the data processor 322 may be equipped to employ AI models in the processing layer 300, AI is not always required. For example, information received from the input side 210 of the interface layer 200 could be in the form of a questionnaire structured according to the schema of the database 410. In that case, the incoming side 310 of the processing layer 300 will assign the questionnaire answers to the appropriate data fields of the structured database 410 by string matching. That data may then be used to generate an outcome that is a simple plot of the timewise trend of a particular data field of the database 410, in which case the outgoing side 312 of the processing layer 300 will simply generate the plot for display at the output side 212 of the interface layer 200.

It should be understood that the data processor 322 may be more than a single machine such that information and data processing may be performed simultaneously by more than one processor of more than one computer with access to the same network (e.g., the internet). In some embodiments, the incoming side 310 and the outgoing side 312 of the processing layer 300 are embodied by distinct computers or networks of computers, as the AI model or other algorithms used to process incoming information may be different from those processing outgoing information. In some embodiments, the incoming side 310 and the outgoing side 312 of the processing layer 300 are embodied by the same computer or network of computers. In some embodiments, the interpretation and processing step 314 is performed on a different computer or server than the data extraction step 316. In some of the examples described below, the data processor 322 may process information at the incoming and outgoing sides 310, 312 using one or multiple large language models (LLMs).

The structured database 410 as defined above and may be stored in non-transient memory of the same computer or computers employed by the processing layer 300. Alternatively or additionally, the structured database 410 may exist on computers, servers, or computer or server networks (e.g., cloud storage) dedicated to data storage that the processing layer can access, as such storage does not require the relatively high processing power of the processing layer 300.

Importantly, the pre-defined schema of the structured database 410—i.e., the list of health indicators or data fields for which data is to be included in the database—informs the incoming side 310 of the processing layer for what data to attempt to extract from the incoming information. That is, after the interpretation and processing step 314, in which the incoming information is parsed and understood, the data processor 322 may look within that interpreted information exclusively for relevant data for which there is a data field 414*a-x* in the structured database 410. When relevant data is found, it is extracted and assigned to the appropriate data field 414*a-x* with a time point or other indexing variable (e.g., patient ID, location, etc.). If the interpreted information does not include relevant data, nothing is extracted from the interpreted information. The limitations of the schema of the database 410 thus provides an element of efficiency to the data extraction step 316 because the data processor 322 disregards information for which there is no place in the structured database.

As noted above, the structured database 410 may also include metadata, and the database schema may include data fields dedicated to metadata. An example of metadata field is a permission-to-access field associated with one or more patient healthcare data fields identifying users that are permitted to access the data in that healthcare data field(s) or permitted to generate outcomes using data in that field or set of fields.

The database layer 400 may include additional databases or database information and is not limited to the structured database 410. The database layer 400 may for example store unprocessed incoming information (e.g., original source material such as uploaded document, chat histories, etc.) or partially processed (e.g., parsed and understood) information so that, if additional data fields are added to the structure of the structured database 410 later, information can be extracted for entry into the revised structured database 410. The database layer 400 may for example include an index storing originally uploaded files, raw data, or partially processed information generated at the incoming side 310 of the processing layer 300 (e.g., by an AI model operating in the processing layer) for subsequent data extraction or use. Some examples are provided below.

Figure 4:
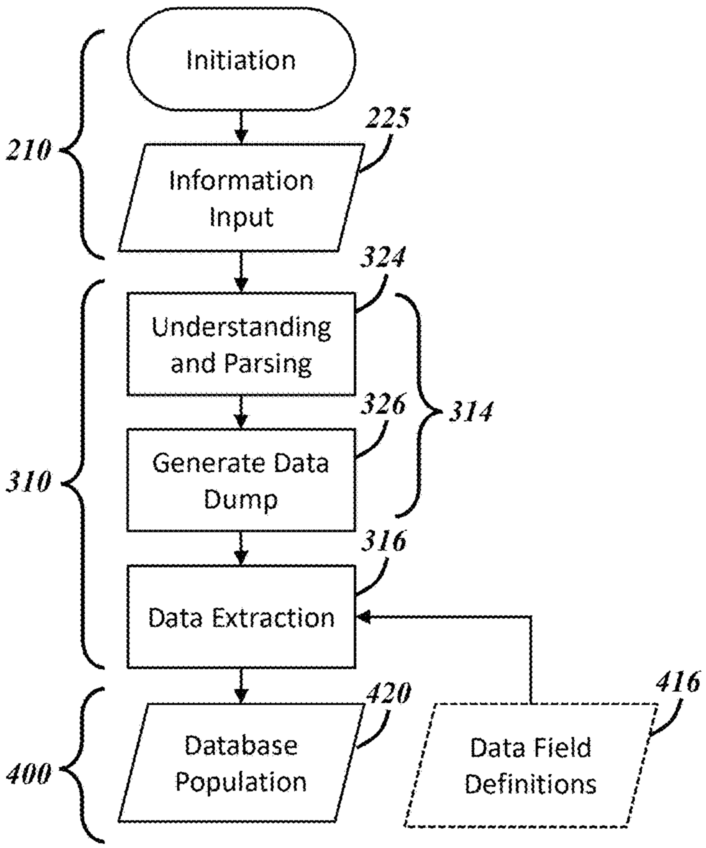
FIG. 4 depicts an example of a data ingestion process of the system.

FIG. 4 schematically illustrates components of an illustrative information ingestion process of the system 100 of FIG. 1, which incorporates the input side 210 of the interface layer 200 and the incoming side 310 of the processing layer 300. The process may be initiated in the interface layer 200 by a user in possession of patient healthcare information, some of which may be unstructured information and/or in multiple different formats, such as text, audio, and various other file formats. The user inputs the information 225 into the system 100 via a user interface, and the system receives the information in the interface layer 200. This step may be performed on a computer via various information collection mechanisms, such as a file uploader, text box, microphone, etc. In some cases, the data ingestion process is initiated by a user interface, which may prompt the user with a question or request the user to finish a questionnaire, etc.

The received information is then interpreted and processed in the processing layer 300, which may employ AI. In this example, the interpretation and processing step 314 includes understanding and parsing the incoming information in step 324 and generating a single data dump in step 326 for subsequent process steps. In the data extraction step 316 in the processing layer 300, the data dump may be searched for relevant data corresponding to the pre-defined data fields 414*a-x* of the structured database 410 (e.g., the columns of the array 412 of FIG. 2). This search of the data dump may also be performed at least in part using an AI model with the data field definitions 416 of FIG. 3 as a possible input. In short, the data field definitions 416 can inform the data extraction step 316 regarding which data in the data dump is relevant data that should be extracted for insertion into the database 410. As discussed above in conjunction with FIG. 3, each data field 414*a-x* may be defined by a plurality of parameters 418 to assist in extracting relevant data from the data dump of processed incoming information. The data extraction step 316 uses the pre-defined data fields 414*a-x* to know what to look for in the data dump from step 326. In the tabular example of the structured database 410 of FIG. 2, the table may include one or more columns or layers of metadata that, strictly speaking, is not patient healthcare data. The metadata may therefore also be included in the data dump search in the data extraction step. The extracted data is then entered into the appropriate fields of the structured database 410 in a database population step 420. Specific examples of data extraction 316 are discussed further below.

In one manner of populating the structured database 410, a structured table format such as that of FIG. 2 is used, where each column has a data field name (e.g., a health indicator or metadata name) and each row corresponds to a time at which a data point or a discrete piece of patient healthcare data is stored in the respective table. For each newly extracted data field value, a new data point may be added to the table as a new row, accompanied by metadata such as a time stamp, source file ID, user ID, or lists of user IDs who are permitted to access the data point. If the search of the data dump yields no information corresponding to the pre-defined data fields, no new row is added to the table and no data fields are populated.

Figure 5:
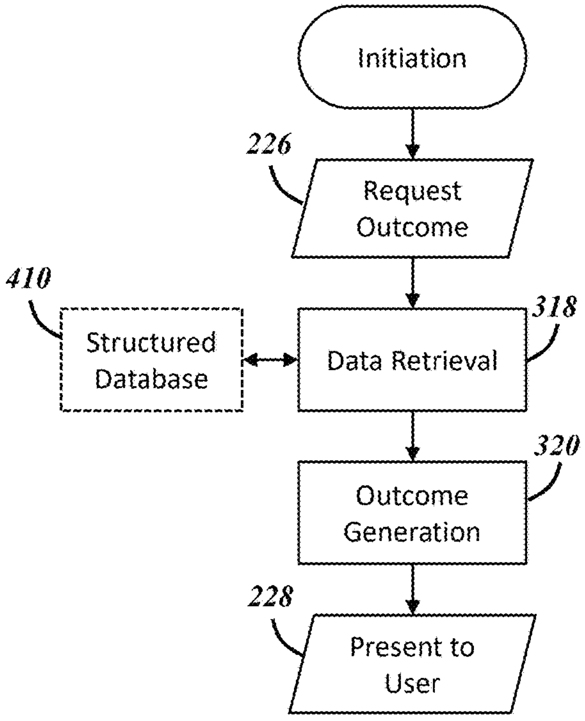
FIG. 5 depicts an example of an outcome generation process of the system.

FIG. 5 schematically illustrates components of an illustrative outcome generation process of the system 100 of FIG. 1, which incorporates the output side 212 of the interface layer 200 and the outgoing side 312 of the processing layer 300. The process may be initiated in the interface layer 200 in a step 226 of requesting an outcome. The outcome may be requested by a user seeking information pertinent to a particular use case, such as by entering a query at a computer of the system network. In some embodiments, the outcome is requested by some other input, such as an automated daily task input associated with a particular use case. Based on the user query or task details received in the request step 226, relevant patient healthcare data is retrieved from the structured database 410 by the processing layer 300 in the data retrieval step 318. This step may be performed by the above-described data processor 322 (FIG. 1), for example. Using the user query or task details and the retrieved data, the requested outcome content is generated in the processing layer 300 in the outcome generation step 320. One or both of these steps 318, 320 may employ an AI model and may be carried out by the above-described data processor 322. As noted above, some outcomes can be generated without AI. The outcome may be generated with a particular format and include particular content defined in the outcome request 226 or with pre-defined content in a pre-defined format for particular outcomes. The outcome is then presented to the user in a step 228 of presenting the requested outcome to the user in the interface layer 200 of the system 100. In addition to or instead of displaying a requested outcome on a display of a computer, requested outcomes may include receipt by a user of a daily reminder based on data in the database 410, the system 100 issuing a health-risk warning message to a provider, a system response to a question (e.g., on-screen, text message, audio alert, etc.), or updating a trend to be displayed on a virtual dashboard, to name a few examples.

FIGS. 6-18 schematically illustrate various examples of aspects of AI-driven processes in the processing layer 300 of the system 100.

Figure 6:
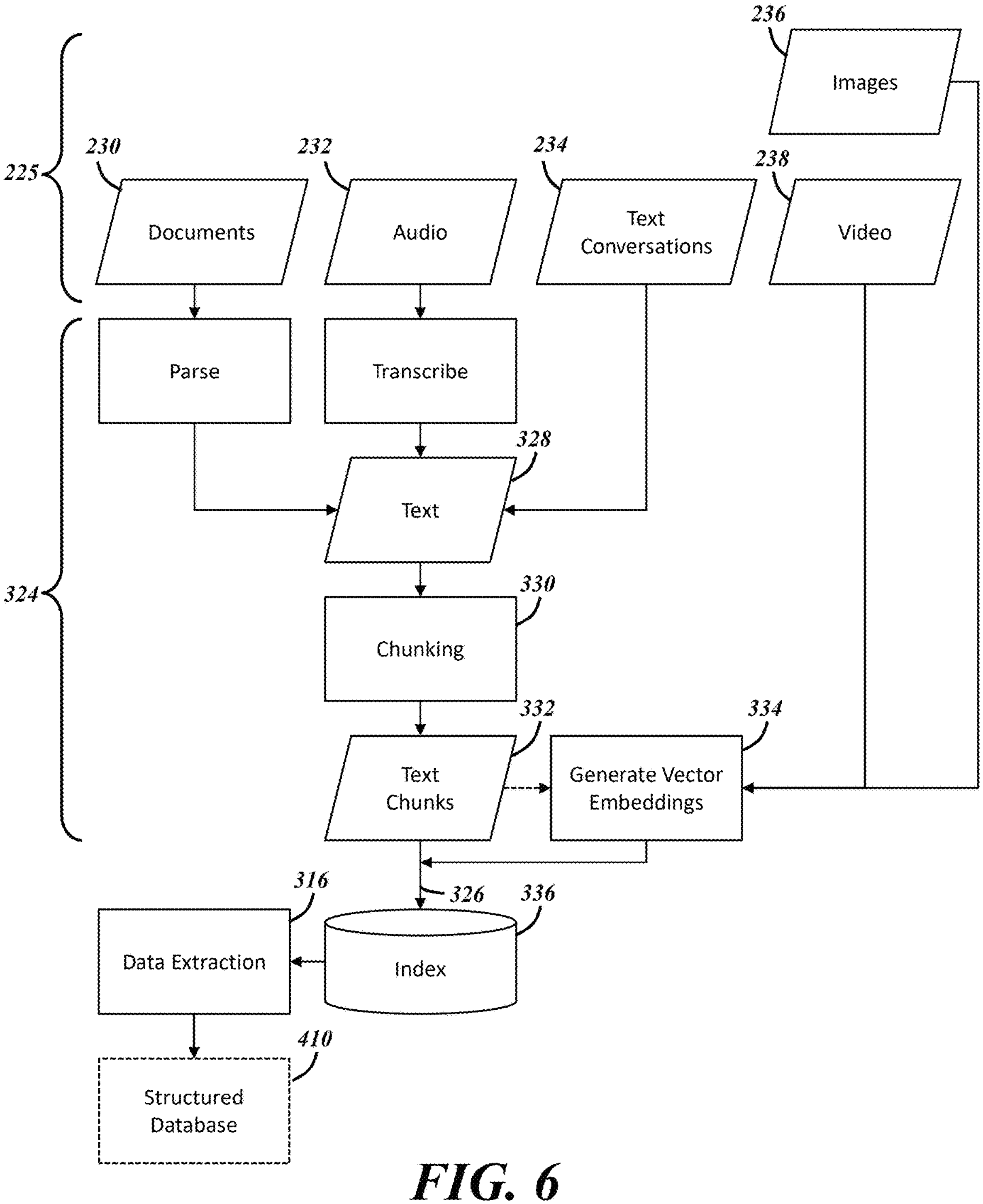
FIG. 6 depicts an example of an incoming information interpretation and extraction process of the system.

FIG. 6 is a diagram schematically illustrating an example of step 324 of FIG. 4, related to understanding and parsing information contained in or derived from patient healthcare information 225 received via the interface layer 200 as shown in FIG. 4. Some of the incoming information is ultimately processed into text from various formats including, in this case, from documents 230, audio information 232, and text conversations 234. Some of the incoming information may include images 236 or video 238. Documents 230 may include word processing documents of various formats, scanned images of documents, or PDF or similar documents. Audio information 232 may include audio files of various formats, such as phone recordings or provider-dictated notes. Text conversations 234 may include emails, email chains, text or SMS logs, or chat session logs. The system 100 is configured to parse incoming information from some of the sources 230-234 and convert the parsed information to text 328 if not already in text format. In some embodiments, the audio portion of video files is processed in the same manner as other audio information. Further text processing may be performed on the resulting text 328, including removal of special characters, lowercasing, etc.

The system 100 is configured to perform a step 330 of chunking on the processed text 328. Chunking 330 involves breaking the text 328 into smaller pieces, or text chunks 332. In some embodiments, the chunking 330 includes semantic chunking, which is based on meaning and context, as opposed to conventional chunking in which text is broken down into smaller pieces based on length or token size. Semantic chunking helps ensure the resulting chunks 330 retain context from the original information sources 230-234. However, any chunking method may be used here. The chunking step 330 may employ an AI model. The text chunks 332 may be included directly in the data dump generated in step 326, as shown in FIG. 6.

In some embodiments, as indicated by the dashed arrow in FIG. 6, a vector embedding process 334 is performed on the text chunks 332 using a machine learning model (e.g., a deep learning model). The resulting vector embeddings are numerical representations of the text chunks 332 that can be used to help subsequent processes when processing the text chunks. The vector embedding step 334 is not always necessary for the textual information. As discussed further below, more than one type of vector embedding 334 can be generated from text chunks 332, such as text embedding or graph embedding.

In addition to interpretation and processing of some incoming information 230-234 into text 328, text chunks 332, and/or vector embeddings, the system 100 and processing layer 300 may be configured to interpret and process image-based information 236 and/or video-based information 238. Images 236 may include photographs, medical imaging images (e.g., X-ray, CT, MRI), etc., in various different formats. Videos may include recordings of video chat sessions or telemedicine visits, for example. There may be some overlap between documents 230 and images 236, as some documents may be received in image file formats to be parsed for any included text. As shown in FIG. 6, vector embeddings may be generated from incoming images 236 or videos 238 as part of the interpretation and processing step 314. While illustrated in FIG. 6 as a single step, the generation 334 of vector embeddings may include different or additional steps for incoming image and video files 236, 238. For example, different AI models or other algorithms may be employed to generate vector embeddings of image or video files than the techniques used to generate vector embeddings from text chunks 332.

The system and processing layer 300 are configured to generate a data dump as in step 326 of FIG. 4 and to store the data dump in an index 336. The data dump may be a single data dump combining data derived from all of the information sources 230-238 and in this case includes the text chunks 332, the corresponding text, graph, image, and video embeddings, and metadata. As used herein, each individual "data dump" is associated with a collection of healthcare information simultaneously received by the system 100, such as a single data upload, a single conversation session, or a collection of healthcare information collected within a specific time range. The data dump may also include other information used or generated in step 314, such as the raw input information received from the various sources 230-238. The index 336 is a precursor to the structured database 410 and contains relevant data from which the structured database 410 can populated, along with other information not required by the structured database. The resulting index 336 can be queried to search for or filter chunks relevant to pre-defined data fields of the structured database 410. The index 336 may also be searched for information pertinent to user queries. As noted above, not all of the data populating the data fields of the database 410 flows through the illustrated process 314 and may have never been stored in the index 336, such as when the incoming information is already structured according to the database schema or when a user inputs information directly into the database 410.

Figure 7:
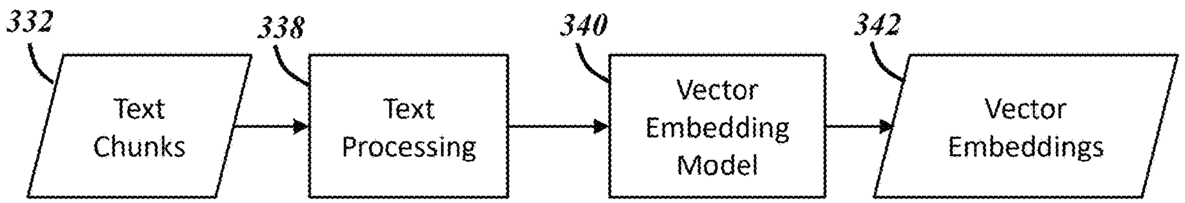
FIG. 7 depicts an example of a text vector embedding process of the system.

FIG. 7 is a diagram schematically illustrating an example of the vector embedding step 334 of FIG. 6, related to generating text vector embeddings from text chunks 332 resulting from understanding and parsing information contained in some of the information sources 230-234 of FIG. 6. The process receives processed text 332 as inputs and generates vector embeddings 342 using a machine learning (e.g., deep learning) vector embedding model 340 to produce dense vector representations as outputs. In some cases, additional text processing 338 is performed on the text chunks 332 prior to generation of the vector embeddings 342. In some embodiments, the generated embeddings 342 in FIG. 7 (stored in the index 336) may be further utilized during the data extraction step 316 in FIG. 9 as part of the Retrieval-Augmented Generation (RAG) method, as further explained in the following description.

Figure 8:
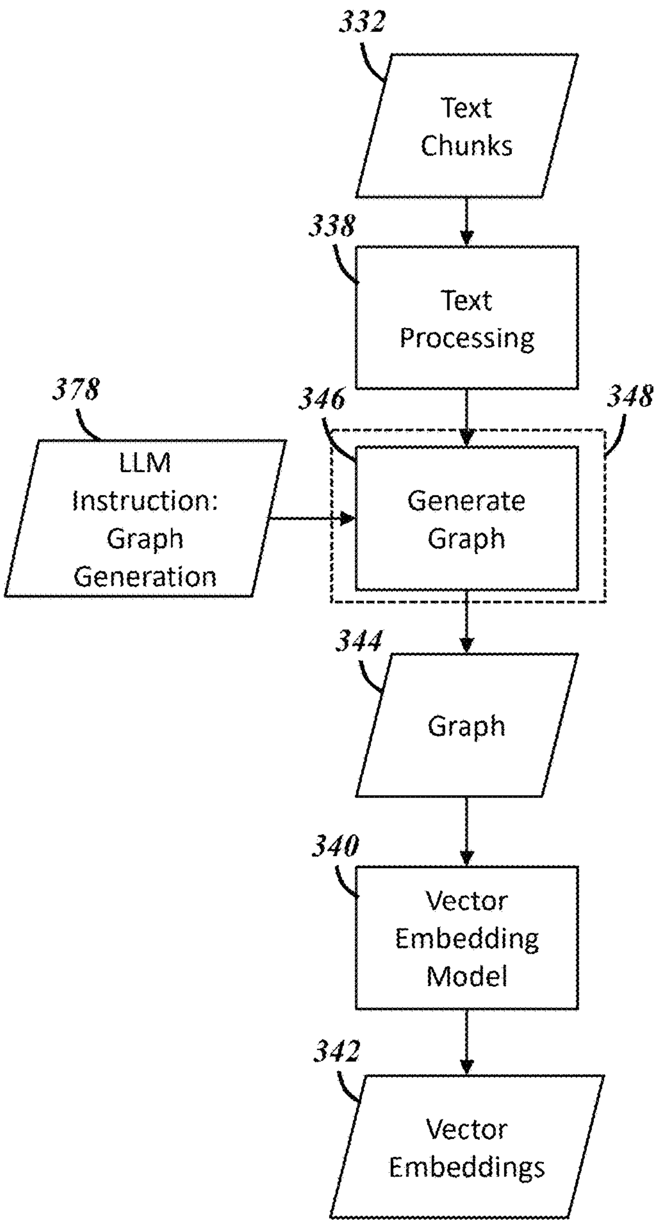
FIG. 8 depicts an example of a graph vector embedding process of the system

FIG. 8 is a diagram schematically illustrating another example of the vector embedding step 334 of FIG. 6. Here, instead of embedding the text chunks 332 directly, a graph 344 is first generated in a graph generation step 346. In this example, a large language model (LLM) 348 is used to generate the graph 344 based on the text chunks 332 as an input and on an LLM instruction 378 including details on how the graph should be generated from the text chunks. A graph includes nodes and/or edges, where nodes represent entities or objects, edges represent relationships or connections between nodes, and entities refer to the real-world objects or concepts that nodes represent. The graph 344 includes nodes and edges extracted from the text chunks 332 by the LLM 348 according to the LLM instruction 378. In this case, the vector embedding model 340 is a graph vector embedding model that produces vector embeddings 342 of the graph nodes and edges to become part of the data dump stored in the index 336 of FIG. 6. As in the text vector embedding process of FIG. 7, additional text processing 338 may be performed on the text chunks 332 to prepare the chunks for the subsequent graph generation and vector embedding steps 346, 340. In some embodiments, the generated graph embeddings 342 in FIG. 8 (stored in the index 336) may be further utilized during the data extraction step 316 in FIG. 9 as part of the GraphRAG method, as further explained in the following description.

Figure 9:
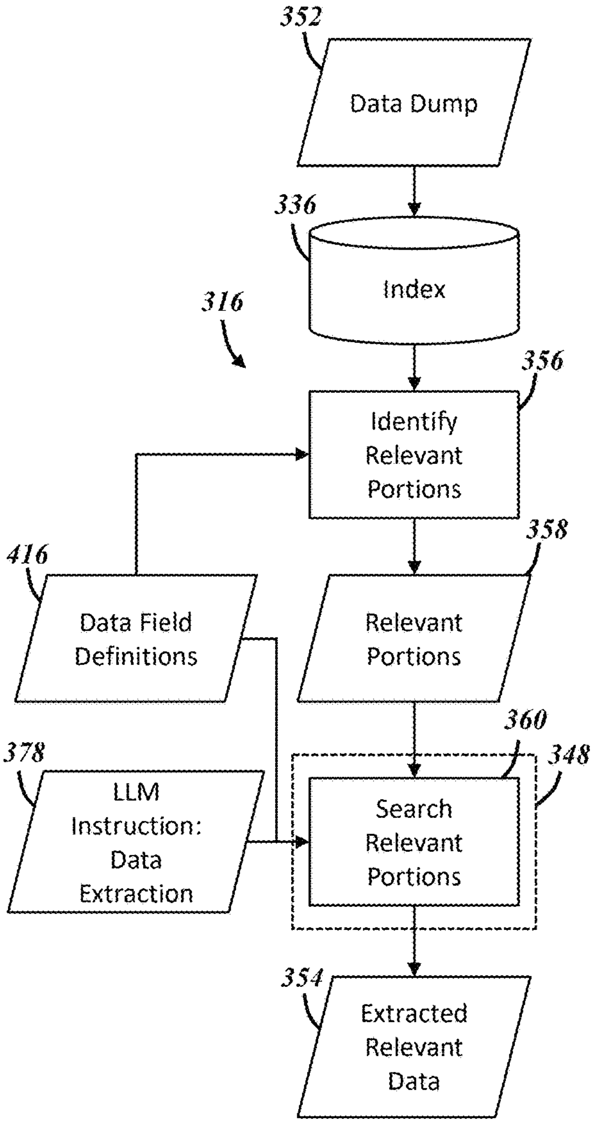
FIG. 9 depicts an example of a data extraction process of the system.
Figure 11:
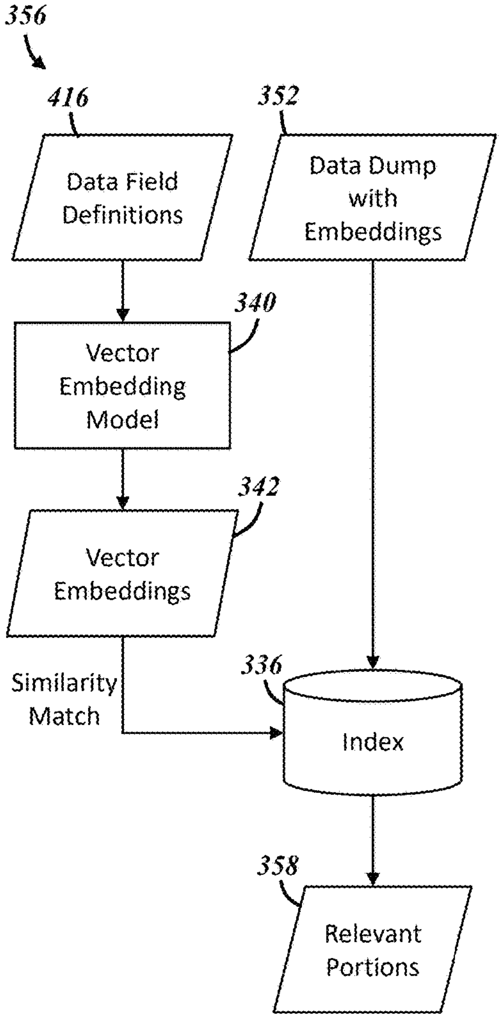
FIG. 11 depicts an example of a portion of the data extraction process for processed information including vector embeddings.

FIG. 9 is a diagram schematically illustrating an example of the data extraction step 316 of FIGS. 1, 4, and 6 on the incoming side 310 of the processing layer 300. Data extraction 316 generally includes searching a newly indexed data dump 352 for relevant data to insert in each of the data fields of the structured database 410. The illustrated process has a single data dump 352 (from step 326) as an input and extracted relevant data 354 as the output. As noted above, the data dump 352 may include any combination of text chunks, vector embeddings (of images, text chunks, and/or graphs), metadata, or other information (e.g., raw source information) stored in the index 336. As shown in the example of FIG. 9, the system 100 and processing layer 300 may be configured to use an LLM 348 to extract relevant data 354 from the indexed data dump 352 for population of the appropriate data fields of the structured database 410. In some cases, the incoming side 310 of the processing layer 300 may apply a RAG method to first identify relevant portions (step 356) within the data dump 352 and then search within the identified relevant portions 358 to extract relevant data 354 for the database 410. RAG is an effective approach for extracting relevant data or answer from large text corpora based on defined data fields or queries. The process starts by identifying the most relevant portions of the input text, assessing their relevance to the target fields or queries. As illustrated in the example of FIG. 11, one approach to determining relevance involves measuring the similarity between the embeddings of defined fields and the embeddings of input text stored in the index 336, including the text embeddings 342 generated in FIG. 7. Alternatively, in some embodiments, a language model can be directly applied to identify relevance without using embeddings, as described in FIG. 12. Other methods to identify relevant portions include but are not limited to keyword search or matching. The identified relevant portions are then provided to a language model alongside the data field definitions or queries, enabling the model to extract and synthesize accurate and contextually relevant responses from the those identified portions.

In embodiments in which the data dump 352 includes graph vector embeddings such as the embeddings 342 generated in FIG. 8, a GraphRAG method—a branch and subset of RAG methods—may be employed. GraphRAG enhances relevant data extraction by structuring knowledge and information as a graph of entities and relationships, enabling better contextual understanding and multi-hop reasoning compared to naïve or vanilla RAG. GraphRAG excels in domains requiring structured, interconnected data retrieval, where entity relationships are crucial. Unlike text embedding-based extraction, GraphRAG, which relies on graph embeddings, identifies relevant portions by measuring the similarity between the embeddings of defined fields and the embeddings of graph (such as node and edge) stored in the index 336 in FIG. 11. This approach enhances the explainability and logical coherence of model responses by leveraging the relational graph. Using GraphRAG is advantageous when dealing with complex, highly connected information where relationships between entities play a key role, such as comprehensive assessment reports where the patient's family member information, social relationships, and historical data are included. Naïve or vanilla RAG, on the other hand, is more suitable for scattered data where simple similarity-based retrieval suffices, such as chat histories or ad-hoc conversation transcripts. In some embodiments, other branches or subsets of RAG method can also be employed to extract relevant data in this system.

The illustrated method, as described in FIG. 9, includes the step 356 of identifying relevant portions 358 of the data dump 352 in which the relevant data 354 is likely to be found and a step 360 of searching within the identified relevant portions 358 of the data dump for relevant data 354 to extract. In the illustrated example, the relevant portions 358 of the data dump 352 are identified in step 356 based on the data field definitions 416 (see FIG. 3). In some embodiments, an LLM 348 is used for step 356, in which case an LLM instruction is needed to check data relevance. Some specific examples of step 356 are discussed in more detail in conjunction with FIGS. 11 and 12. The data field definitions may be defined by a user, or the system 100 can provide pre-defined data fields as default data fields or data field options from which a user can select the desired data fields.

The inputs to the LLM 348 in the example of FIG. 9 include the identified relevant portions 358 from step 356, the data field definitions 416, and at least one LLM instruction 378. It is noted here that, while LLMs are referenced throughout this disclosure using reference numeral 348, same or different LLMs may be employed for various processes, tailored to specific tasks and requirements. For instance, the LLM 348 used for graph generation in FIG. 8 may differ from the LLM 348 used for data extraction in FIG. 9, as the latter task may necessitate an LLM with higher response speed, whereas the LLM used for other tasks could be the same one as the one in FIG. 9. Additionally, while LLM instructions are identified throughout this disclosure using reference numeral 378, the LLM instructions for the various illustrated processes are different and tailored to the specific task and the specific AI model being used. For example, FIGS. 11 and 12 include two different examples of step 356, and only one of those examples requires an LLM instruction 378. That instruction is different from the data extraction instruction 378 in FIG. 9. While not shown explicitly in FIG. 9 or in other figures illustrating an LLM instruction, the data processor may perform an intermediate step of integrating the LLM instruction 378 with additional inputs for LLM 348 (such as the data field definitions 416) by embedding them into a predefined LLM instruction template 362. The instruction 378 defined in the template 362, along with other inputs inserted into the template, will collectively form a complete input to the LLM, as further discussed below.

Figure 10:
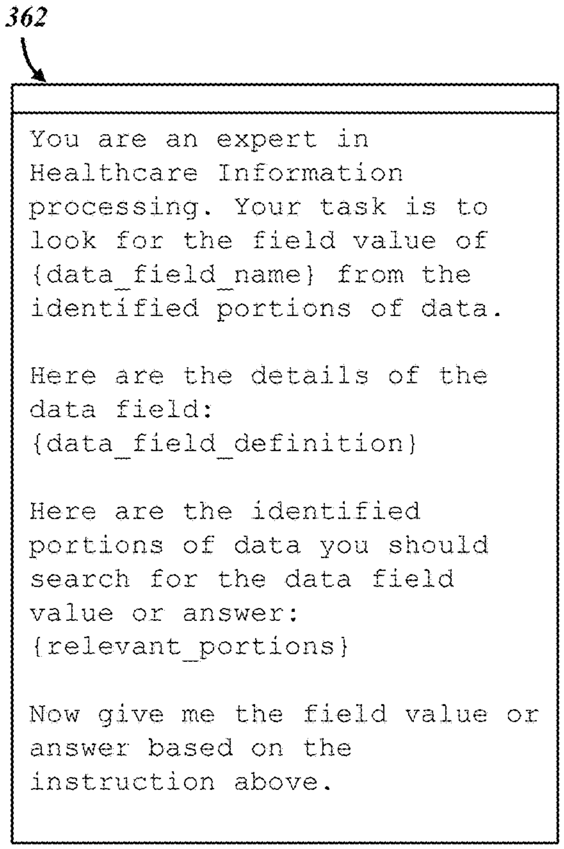
FIG. 10 depicts an example of an LLM instruction template.

FIG. 10 is a non-limiting example of an LLM instruction template 362 where the LLM instruction 378 and entries to other LLM inputs of FIG. 9 are included. The template 362 contains the instruction 378, formulated in language similar to what a human user would use to interact with LLM 348 for searching relevant data 354. However, this template 362 and the included LLM instruction 378 are invisible to system users, as the templates may be pre-defined and stored in non-transient memory of the data processor 322 (FIG. 1) performing the illustrated steps.

Using the heart rate data field 414*b* of FIGS. 2 and 3 as an example, the LLM instruction template 362 involves inserting “heart rate” in the {data_field_name} entry of the template, the data field definition 416*b* in the {data_field-_definition} entry of the template, and the relevant portions 358 of the data dump identified in step 356 in the {relevant-_portions} entry of the template. This is of course only one example of an instruction template, the language of which may be tailored to the particular LLM being employed and the entries of which may be more or less or different than in the example. In this case, templates are generated and filled for each pre-defined data field of the database 410 and fed to the LLM 348 to find relevant data 354 for extraction and database population.

The extracted data 354 for each data dump may be limited to values or answers for one or more of the pre-defined data fields of the structured database 410, including patient healthcare data and metadata. If no such values or answers are found, then no data is extracted and no change is made to the structured database 410. The data extraction process 316 may be triggered with each new occurrence of a data dump 352, and the search of each data dump may be limited to the specific data dump triggering each search. The index 336 may, for example, include multiple data dumps from previously received and processed incoming information. While these data dumps may be useful in other processes beyond the illustrated data extraction process 316, only new data dumps from which data is to be extracted and have not yet been searched for data to extract are searched in steps 356-360.

FIG. 11 is a diagram schematically illustrating one example of the step 356 of identifying relevant portions 358 of the data dump 352 in which to search for relevant data 354 for extraction. The illustrated process may be used when the data dump 352 includes vector embeddings 342 (FIGS. 7 and 8), such as text embeddings or graph embeddings. In general, this version of step 356 generates vector embeddings 342 based on the data field definitions 416 and uses them to identify the relevant portions 358 of the data dump 352 in the index 336 in which to search for the relevant data 354 in step 360 of FIG. 9. Here, the data field definitions 416 are first converted to embedding vectors 342. These embeddings 342 are then used to search for similar embeddings in the indexed data dump 352. The system 100 and processing layer 300 may be configured to return the top K similar portions from the index 336 as relevant portions 358, where K is the number of portions with embeddings the most similar to the embedding vector of the data field definition. Thresholding methods other than top K could be used.

The same process 356 may be used with text embeddings or with graph embeddings of the data dump 352. The difference is that a naïve or vanilla RAG method may employ the similarity matching with text embeddings, while a GraphRAG model may find the most similar node and edge information using graph embeddings to identify the relevant portions 358 of the data dump 352. It is noted that the version of the identification step 356 illustrated in FIG. 11 does not employ the LLM 348 or an LLM instruction.

Figure 12:
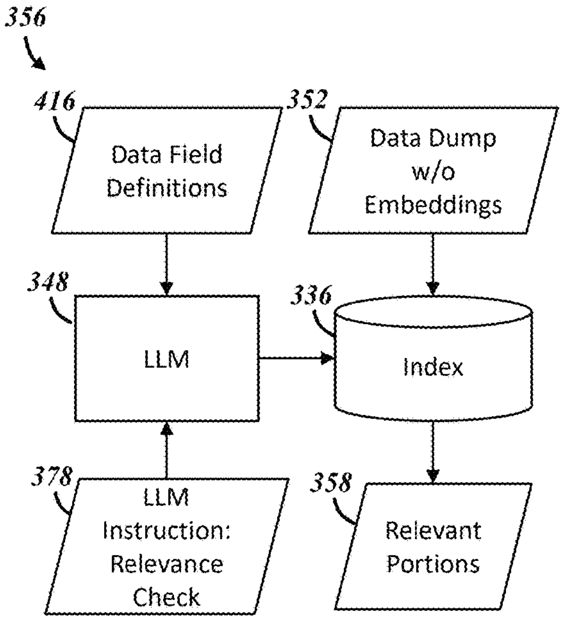
FIG. 12 depicts an example of a portion of the data extraction process for processed information without vector embeddings.

FIG. 12 is a diagram schematically illustrating one example of the step 356 of identifying relevant portions 358 of the data dump 352 in which to search for relevant data 354 for extraction when the data dump 352 does not include any vector embeddings 342, such as when the data dump only includes the text chunks 332 of FIG. 6. Here, the LLM 348 may be used directly to find relevant portions (e.g., text chunks) 358 in the index 336 with the data field definitions 416 providing the information upon which relevance is to be determined. The system 100 and processing layer 300 may be configured to return the top K similar chunks from the index 336 as relevant portions 358, where K is the number of chunks the most similar to the data field definition. Here, the LLM relevance check instruction 378 is different from the LLM instruction 378 in the example of FIG. 9 because the LLM 348 is performing a different task. Specifically, it is asked to find the most relevant portions 358 of the data dump 352 rather than to extract relevant data (e.g., values or answers) 354 from already-identified relevant portions 358 of the data dump. While not shown explicitly in FIG. 12, the LLM instruction 378 for the relevance check may be defined in a template with entries populated with parameters from the data field definitions 416.

Figure 13:
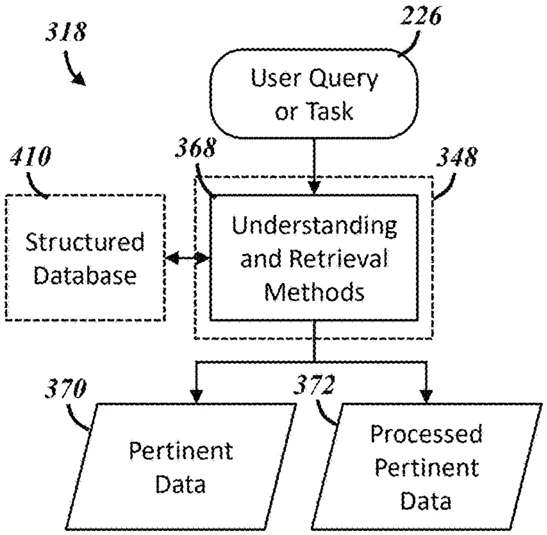
FIG. 13 depicts an example of a data retrieval process of the system.

FIG. 13 is a diagram schematically illustrating an example of the data retrieval process 318 of FIG. 5 involving the outgoing side 312 of the processing layer. The process is initiated by a request 226, which may be a user query or a scheduled task with the query or task details as an input. The user, or the system 100 when a task is scheduled to be executed by the system, may request an outcome (226 in FIG. 5), for example. The system and processing layer 300 may be configured to use one or more LLM understanding and retrieval methods 368 to understand the request 226, retrieve pertinent data 370 from the structured database 410, and output the pertinent data or processed pertinent data 372. As used herein, “pertinent data” is a subset of the relevant data 354 stored in the structured database and is defined as data that is pertinent to the request 226. Processed pertinent data 372 is the outcome of the outcome request 226 and may include a summary of the pertinent data 370, an analysis of the pertinent data, or insights based on the pertinent data. Illustrative methods for LLM understanding and retrieval based on data from the structured database 410 include, but are not limited to Text2SQL, chain-of-table, single-step LLM understanding, or table-augmented generation (TAG).

In the Text2SQL method, the LLM 348 generates SQL queries and executes them over the structured data to obtain the pertinent data 370. In the chain-of-table method, the LLM 348 receives the entire structured database 410 (e.g., as a table) as an input and applies operations on the table to extract pertinent data from which to provide summaries, insights, analyses, or other processed relevant data 372. In single-step LLM understanding, the entire structured database 410 and the request details are fed into an LLM at once, allowing the LLM to extract pertinent data and generate summaries, insights, and analyses in one step. In the TAG method, the LLM generates summaries, insights, analyses, etc. based on the request details and data retrieved by other methods. As used here the "entire structured database" may be either the entire array 412 of data 414 for an individual patient or the entire array of data for all patients in the database 410.

Figure 14:
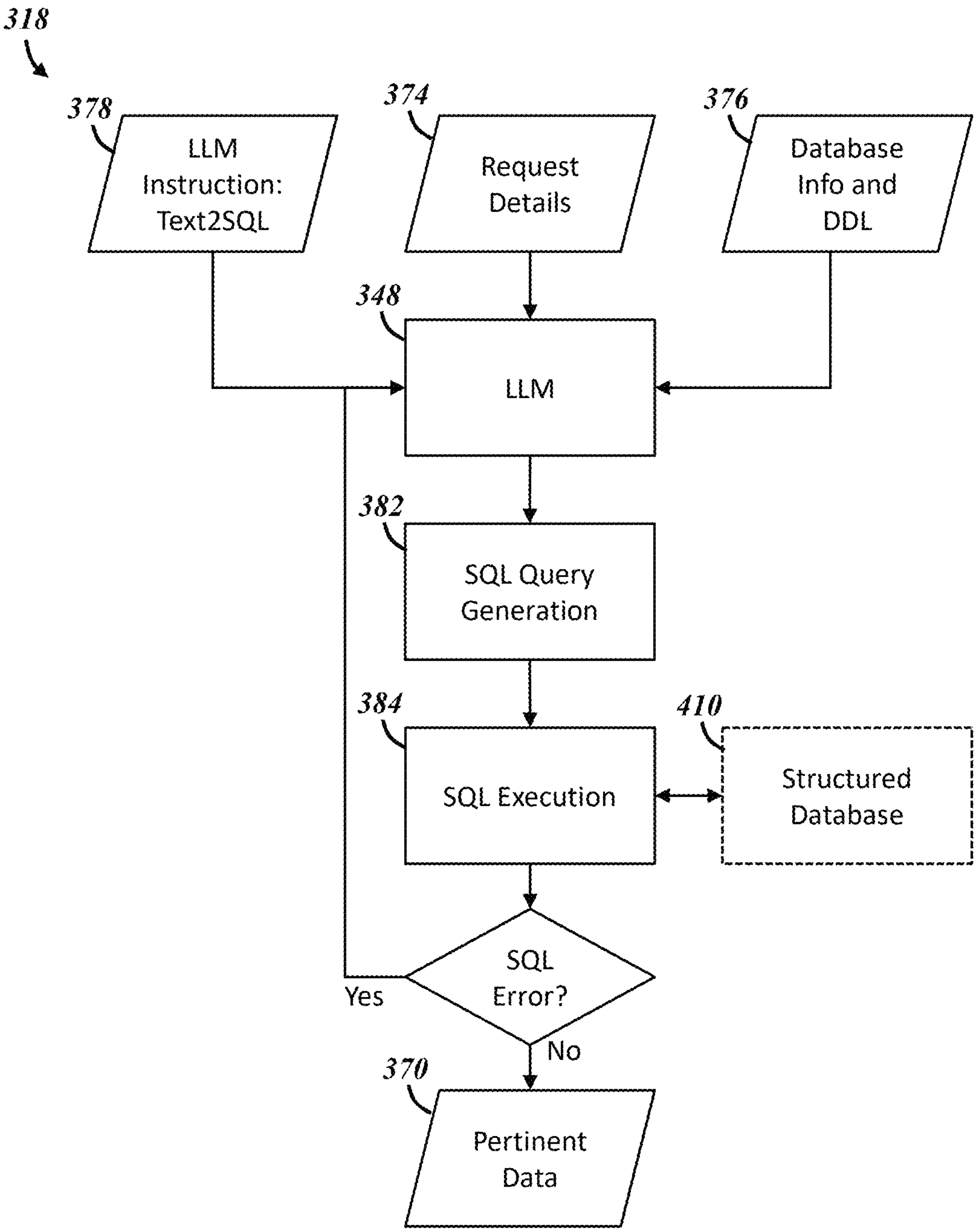
FIG. 14 depicts an example of a data retrieval process using a Text2SQL method.

FIG. 14 is a diagram schematically illustrating an example of the data retrieval process 318 using the Text2SQL method. Inputs to the LLM 348 may include details 374 from the user query 226 and/or other request details 374, database information and data definition language (DDL) 376, and an LLM instruction 378. The LLM instruction 378 may be defined in a template including entries to be populated with request details 374 and/or the database info and DDL 376. The LLM 348 generates an SQL query (step 382) based on the instruction 378 to retrieve pertinent data 370 from the structured database 410. The SQL query is then executed on the structured data 410 (step 384). The outcome of the SQL execution step 384 is the pertinent data 370. If the SQL query execution 384 returns an error, an error message along with extra instructions for error correction and other LLM inputs are fed back into the LLM 348 to generate a new SQL query 382. The process is repeated until the SQL query executes without an error or the maximum limit of executions is reached.

Figure 15:
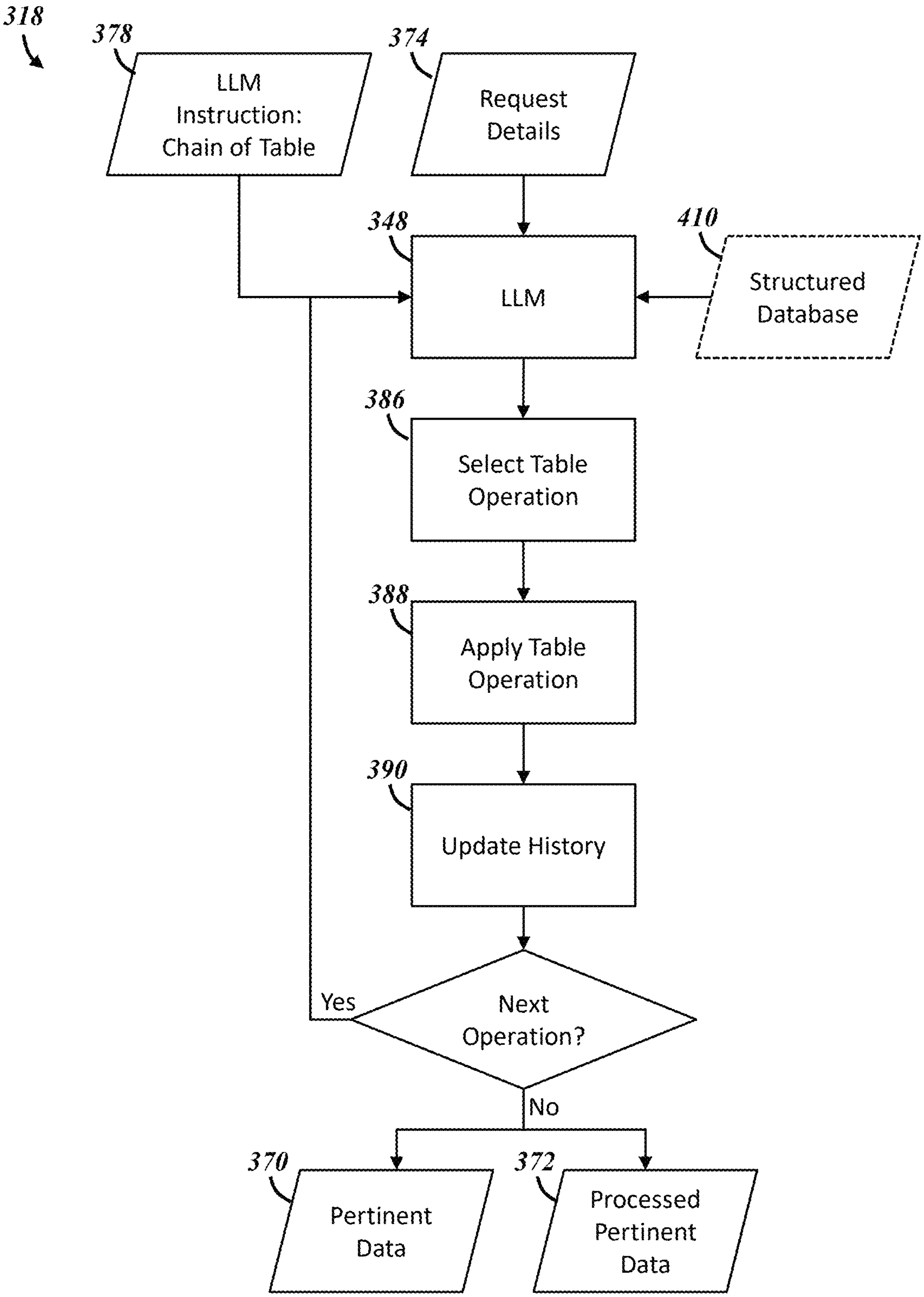
FIG. 15 depicts an example of a data retrieval process using a chain-of-table method.

FIG. 15 is a diagram schematically illustrating another example of the data retrieval process 318 using the chain-of-table method. Here, the request details 374, the entire structured database 410, and a chain-of-table LLM instruction 378 are fed into the LLM 348. As with other LLM instructions, the chain-of-table instruction 378 may be included in a pre-defined template having entries that are populated with information from the other inputs to the LLM 348. The LLM 348 selects a table operation from a finite group of options (step 386). In one embodiment, there are five options, including: adding a column, selecting rows, selecting columns, grouping by, or sorting the table. The selected table operation is then applied to the table (step 388), and the table (i.e., database 410) is updated accordingly, along with the table update history (step 390). The LLM 348 reviews the table update history and decides whether to select the next table operation or determine that no further operations are needed. If the LLM 348 determines no more table operations are necessary, the LLM generates summaries, insights, and analyses or other processed pertinent data 372 based on the last updated table, with the table also serving as pertinent data 370.

Figure 16:
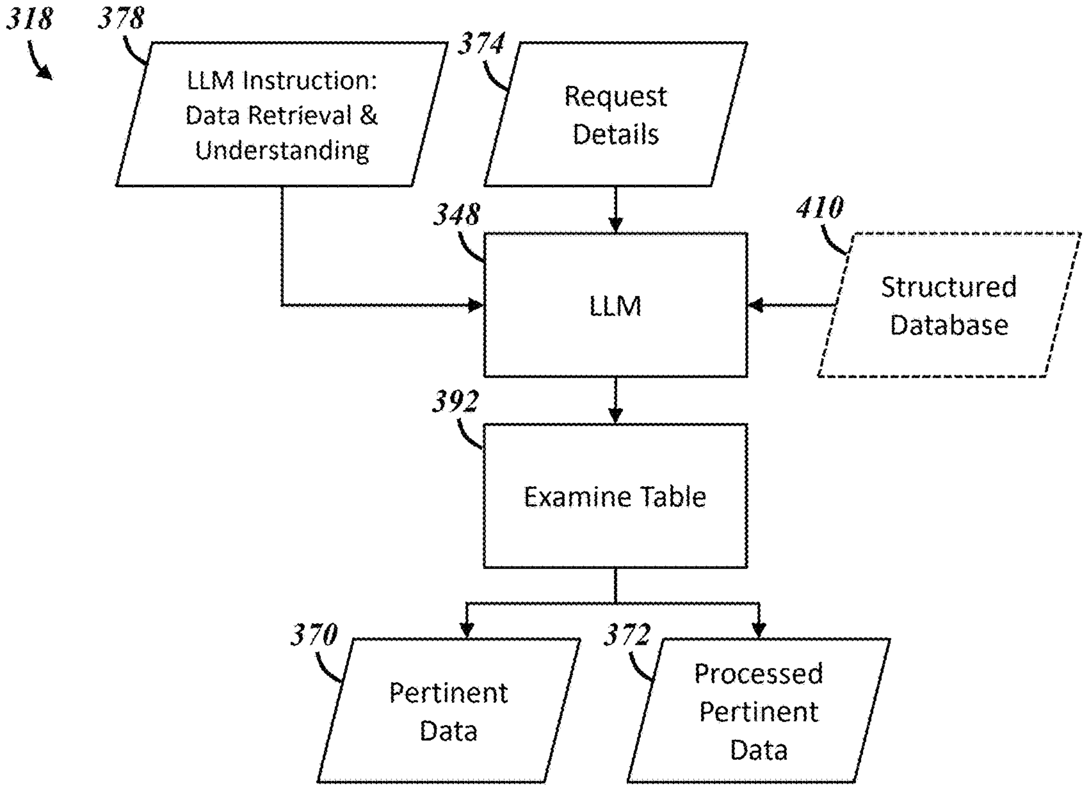
FIG. 16 depicts an example of a data retrieval process using a single-step LLM understanding method.

FIG. 16 is a diagram schematically illustrating another example of the data retrieval process 318 using the single-step LLM understanding method. Here, the request details 374, the entire structured database 410, and a data retrieval and understanding LLM instruction 378 for pertinent data selection and for processing of the pertinent data (e.g., summary, insight, or analysis) are fed into the LLM 348. The LLM 348 examines the entire database 410 directly (step 392) to determine the pertinent data 370. The LLM 348 may simultaneously generate summaries, insights, and/or analyses 372 based on the identified pertinent data 370.

Figure 17:
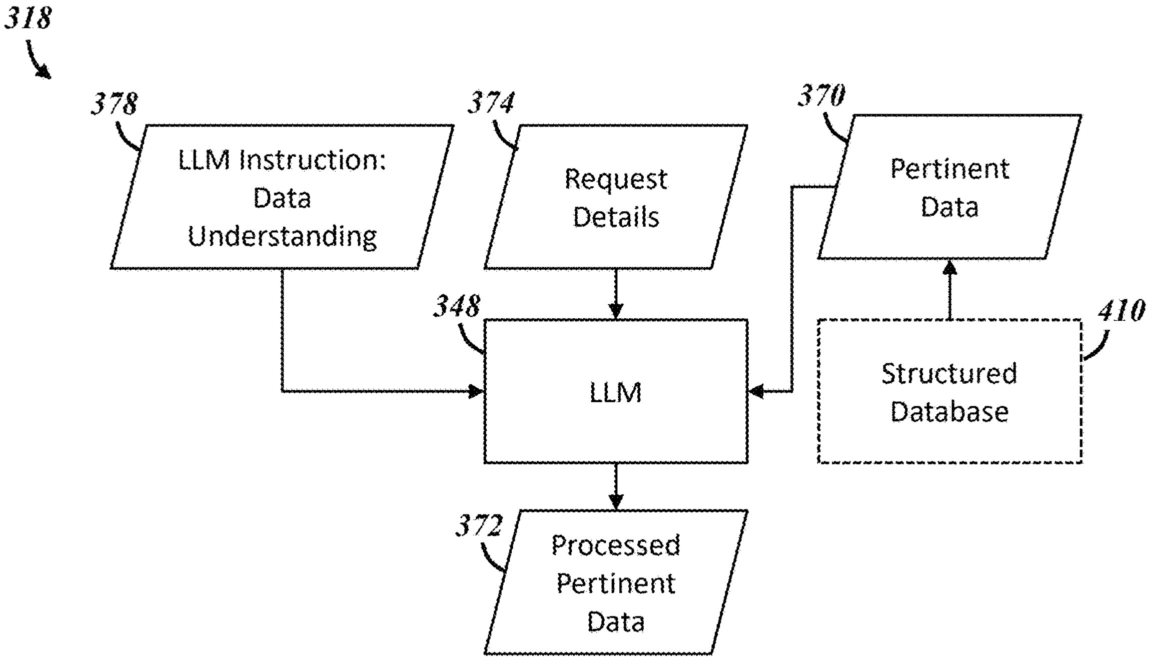
FIG. 17 depicts an example of a data retrieval process using a table augmented generation (TAG) method.

FIG. 17 is a diagram schematically illustrating another example of the data retrieval process 318 using the TAG method. Here, in addition to the request details 374 and LLM instruction 378, the pertinent data 370 retrieved by other methods (e.g., other LLM methods such as, Text2SQL, chain-of-table, or single-step LLM understanding) are fed into the LLM 348 to generate additionally processed pertinent data 372, such as visualizations, trends, or predictive analytics.

Figure 18:
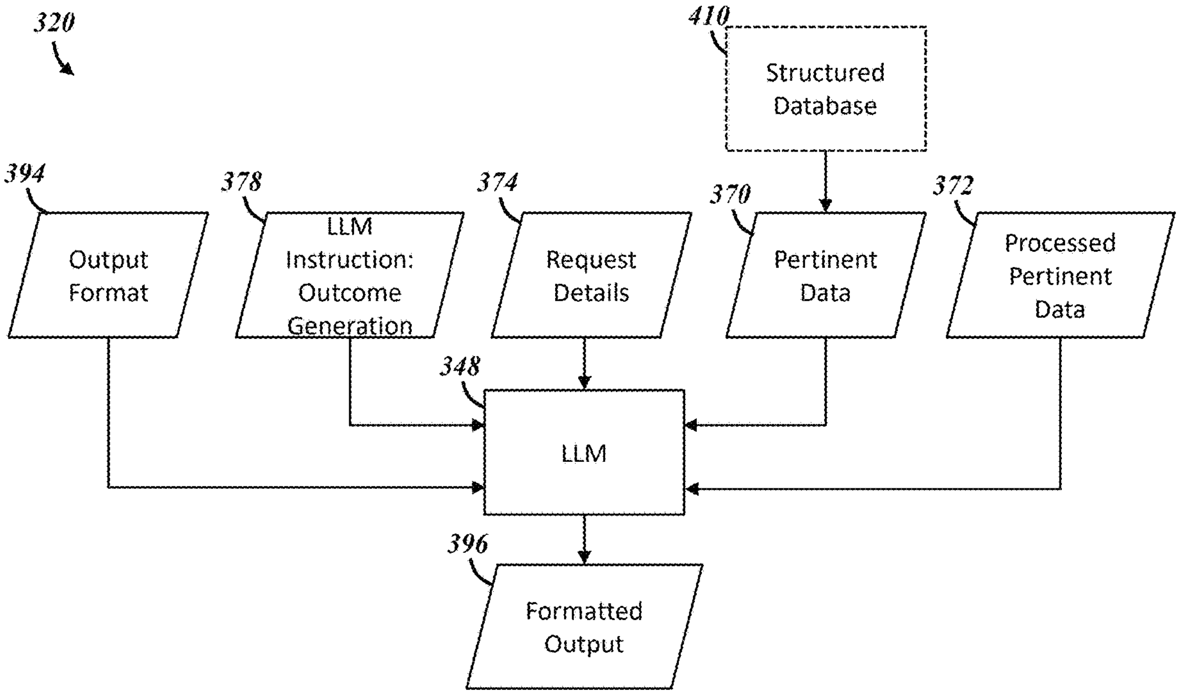
FIG. 18 depicts an example of an outcome generation process of the system.

FIG. 18 is a diagram schematically illustrating an example of the outcome generation process 320 (FIGS. 1 and 5). Here, the request details 374, the pertinent data 370 and processed data 372 from the data retrieval process 318, and an outcome generation LLM instruction 378 along with output format instructions 394 are fed into the LLM 348. The LLM 348 generates a final formatted output or response 396 for presentation to the user (step 228, FIG. 5) in the interface layer 200 according to the specific format and requirements of the outcome request 226.

Figure 19:
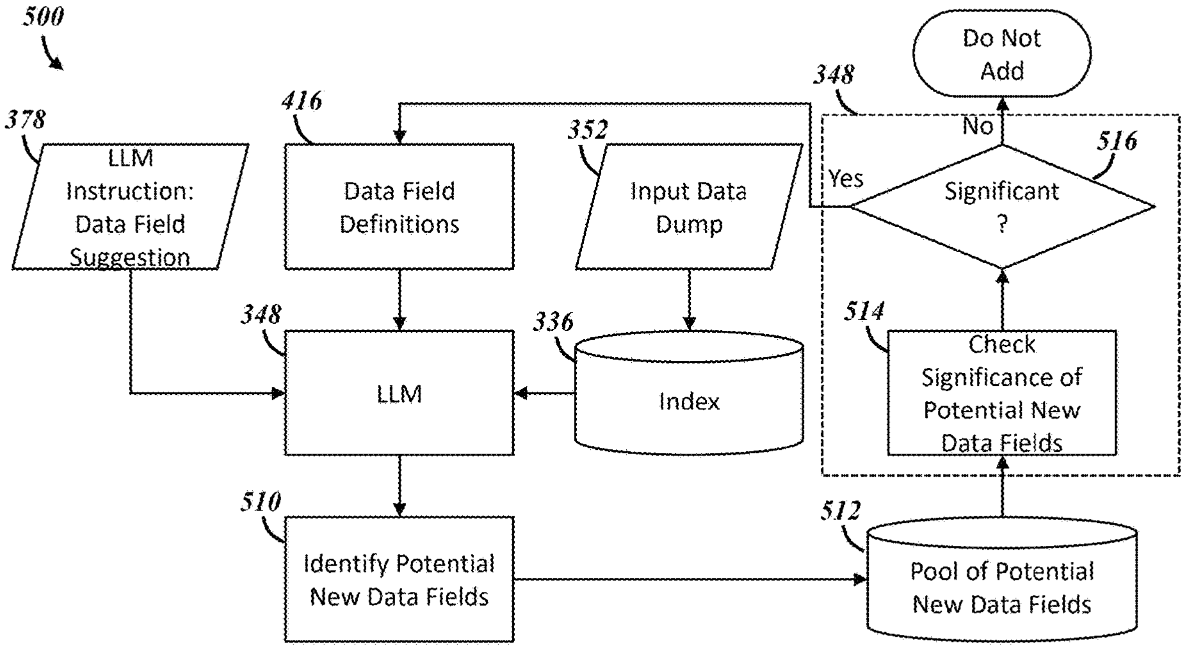
FIG. 19 depicts an example of a database adaptability process of the system.

The system 100 may be configured with a database adaptability mechanism in the processing layer 300 and may be configured to perform a database adaptability process 500, an example of which is illustrated schematically in FIG. 19. In the adaptability process 500, processed input information (documents, images, text, etc.) is examined using AI models or applications to determine whether any new data field(s) could be defined for the structured database 410. Here, the LLM 348 identifies potential new data fields from the input information 225 (FIG. 4) (step 510) after that information is interpreted and processed during information ingestion and compares them with the present data field definitions 416. Each identified potential new data field that is not identical or similar to an already-existing data field is stored in a pool of potential new data fields 512. While defining a potential new data field, the LLM 348 may use the same data field parameters 418 as the pre-defined data fields (e.g., field name, units, format, etc.) provided in an LLM instruction 378 for data field suggestion. As with other LLM instructions, this instruction may also be defined in an instruction template with entries populated with information from other inputs to the LLM 348.

The LLM 348 may regularly review the pool 512 to evaluate whether any of the potential new data field candidates are significant enough to be added as pre-defined data fields of the structured database 410. For example, each time a data dump 352 is added to the index 336 a significance check (step 514) of the potential new data fields in the pool 512 may be triggered. If the same potential new data field continues to appear in additional data dumps 352, that potential data field may be deemed sufficiently significant (step 516) to add to the data field definitions 416 as a new data field. In some cases, the system automatically adds new data fields via this process based on a pre-defined significance threshold (e.g., the number of instances per unit time the potential new data field appears in data dumps). In other cases, the significant potential new data field is presented to a user to verify or deny the addition of the data field. The LLM may, for example, prompt a user in the interface layer 200 to inform the user about a potential new data field that has been determined to be potentially valuable and receive an instruction from the user as to whether the new data field should be added. Subsequent information ingestion processes will use the updated data field definitions 416 in the above-described processes that use the data field definitions.

Figure 20:
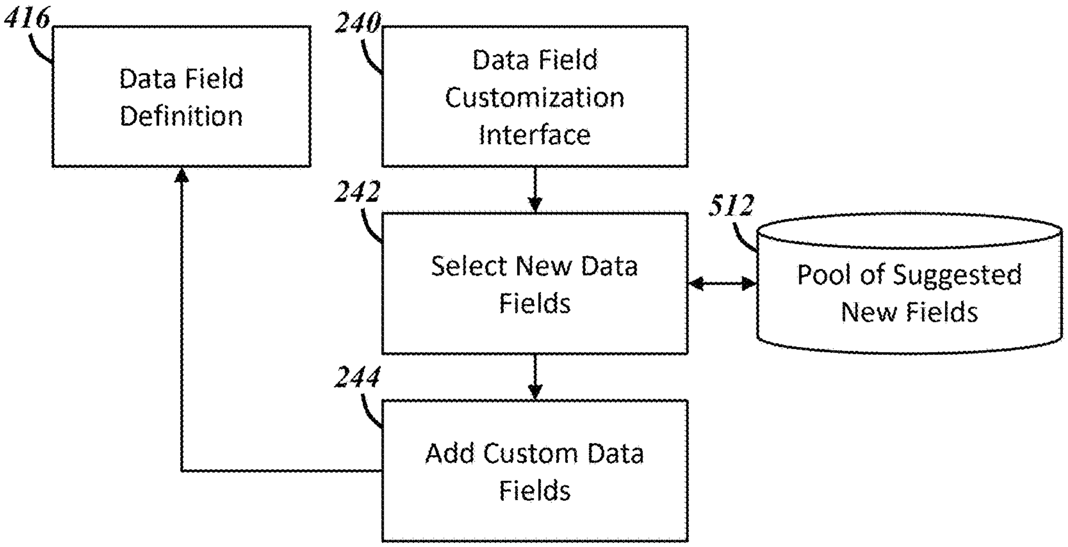
FIG. 20 depicts an example of a database customization and configuration process of the system.

FIG. 20 is a diagram schematically illustrating an example of a database customization and configuration process in which a user can customize the pre-defined data fields of the structured database 410. For example, the pre-defined data fields 414*a-x* (FIG. 2) may be displayed to a user in the interface layer 200 of the system 100 along with a list of potential new data fields collected by the LLM via the database adaptability process 500 of FIG. 19. Or, a user can simply create one or more new data fields to be added to the database schema with corresponding data field definitions 416. This may occur via a customization interface 240 such as a software module running on a computer in the interface layer 200, for example. System-suggested parameters for the each potential new data field (e.g., field name, unit, format) may be presented, or a user can define their own parameters via the same interface 240. The user can select new data fields from the pool of suggested new fields 512 (step 242) and/or add custom data fields (step 244) and their associated parameters to the pre-defined data fields of the structured database. The next time the system 100 receives patient healthcare information, the information will be processed as before with the data extraction process now configured to find data relevant to the new data field and other existing data fields. In some embodiments, the previously received data dumps stored in database 400 will be reprocessed using the data extraction process, now configured to identify data relevant to the new data field.

Figure 21:
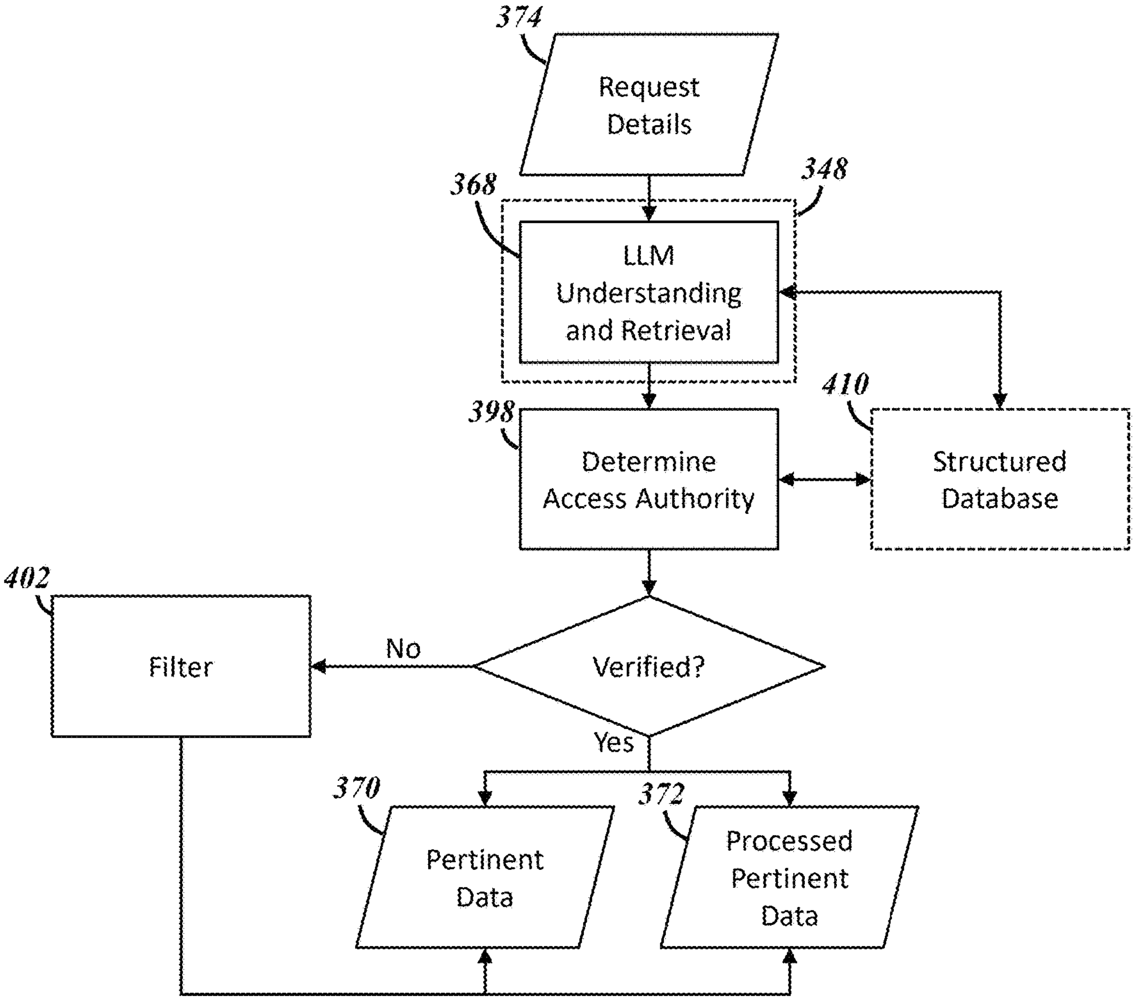
FIG. 21 depicts an example of a user authentication and access control process of the system.

FIG. 21 is a diagram schematically illustrating an example of a user authentication and access control process by which a user's access permission is verified before the data retrieval process 318. In one manner of operation, the structured database 410 includes metadata for each data point, for each data field, or for each category of data in the database, and the metadata includes or is an indicator of one or more individuals or entities who are permitted to access that data point, data field, or category of data. The illustrated example uses the process of FIG. 13 as its basis but adds a verification loop after the LLM understanding and retrieval step(s) 368. The verification loop includes determining which data in the structured database 410 the user providing the request is authorized to access (step 398), such as by checking the metadata associated with the pertinent data 370. If the user is authorized to access all of the pertinent data, then the pertinent data 370 and/or processed pertinent data 372 is presented to the user. If the user is not authorized to access all of the pertinent data, then the pertinent data 370 is filtered (step 402) prior to its presentation and the presentation of any processed relevant data 372. The filtering step 402 may omit the portion of the pertinent data 370 the user does not have access to or simply not return any pertinent data in response to the request. In other examples, the verification loop is located between the request details 374 and the LLM 348 such that the user's access authority is checked before the outcome request gets that far. If the user does not have access authority for the requested data 370, then nothing further is done—i.e., the understanding and retrieval step 368 is not initiated.

Following are a variety of use cases for the disclosed system 100, which are intended to be non-limiting examples.

One use case is related to insurance company analytics. In this example, the user may be an insurance company and its agents. The data sources for populating the structured database may include patient healthcare information 225 (FIG. 4) entered into the healthcare information management system 100 by various healthcare providers. The healthcare information 225 received by the healthcare information management system 100 may include uploaded health reports 216 (e.g., medical records, lab results), uploaded assessment documents 230 (e.g., standardized assessments, care plans), phone call transcripts between patients and providers, chat histories from patient-provider communications 234, and/or photos or images 236 uploaded by patients (e.g., medication pictures, wound images), to name a few sources. At least some of this received information 225 may be unstructured. Illustrative system outputs or outcome requests in this use case may include items such as a comprehensive dashboard displaying trends in quality of life measurements (e.g., blood pressure, ADL/iADL scores, hospital visits, etc.) for one or more patients with healthcare data in the database 410, predictive analytics identifying potential health risks among patient populations, reports highlighting areas for intervention to improve overall patient outcomes, or alerts for metrics that are approaching thresholds tied to regulatory penalties or incentives.

Another use case is related to report generation and documentation. In this example, the users may be healthcare providers (e.g., nurses or case managers). The sources of input information 225 for populating the structured database 410 may include data that are already stored in the providers' respective hospital or nursing system. The healthcare information 225 received by the healthcare information management system 100 may include already-existing information on historical health conditions, patient health reports 216, after-visit summaries, doctor notes and prescriptions, patient information in the hospital or nursing data management system or API data, and/or uploaded assessment documents and previous care plans. At least some of the incoming information may be unstructured. In response to provider outcome requests 226 specifying output report requirements 374, illustrative system outputs (e.g. processed pertinent data 372) in this use case may include items such as automated generation of health assessment reports tailored to specific patients, AI-generated Plans of Care (PoC) that comply with regulatory standards, summarized patient history, diagnoses, treatment plans, and prognoses, or visualizations such as graphs and charts to aid in understanding patient data.

Another use case is related to caregiver management. In this example, the users may be caregivers or healthcare administrators. The data sources 225 for populating the structured database 410 may include scheduling systems, caregiver profiles, and/or training modules. The healthcare information 225 received by the healthcare information management system 100 may include shift schedules and updates, notifications for training or policy changes, or real-time reporting from caregivers via voice or text, to name a few sources. At least some of the incoming information may be unstructured. Illustrative system outputs or outcomes 372 in this use case may include items such as automated shift coordination and notifications sent via SMS or voice calls, delivery of training modules and updates through outbound communications, logs of caregiver reports linked to patient records in the database, or alerts for missed shifts or compliance issues requiring administrative attention.

Another use case is related to family communications, in which the users may be family members of patients with healthcare data in the structured database 410. The data sources 225 for populating the structured database 410 may include patient status updates, care plan changes from the provider side, and/or existing patient health knowledge base in the database. At least some of the incoming information may be unstructured. The healthcare information 225 received by the healthcare information management system 100 may include scheduled notifications about appointments or care activities or authorization information for accessing the patient's healthcare data. Illustrative system outputs or outcomes 372 in this use case may include regular health reports and risk analysis reports with pre-diagnosis of the patient for the sake of preventive care, regular updates on patient status and well-being according to the patient health indicators, or notifications about upcoming appointments or changes in care plans.

Another use case is related to personal assistance for patients, in which the patients with healthcare data in the structured database 410 are the users. The data sources 225 for populating the structured database 410 may include patient profiles, self-reported data, and/or existing patient health knowledge base in the database. The healthcare information 225 received by the healthcare information management system 100 may include authorization information for accessing the patient's healthcare data, voice commands and interactions with a voice-agent interface, or preferences for entertainment and educational content, to name a few examples. At least some of the incoming information 225 may be unstructured. Illustrative system outputs or outcomes 372 in this use case may include regular health reports and risk analysis reports with pre-diagnosis to the patient for the sake of preventive care, daily routine health assistance, health care suggestions, lifestyle/diet suggestions and tips through reminders and texts, regular health educations via automated calls or texts, personalized social interaction and chat based on patient database to reduce feelings of loneliness (e.g., conversational engagement), or access to personalized entertainment or educational materials via voice requests.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation. In addition, the term "and/or" is to be construed as an inclusive OR. Therefore, for example, the phrase "A, B, and/or C" is to be interpreted as covering all the following: "A"; "B"; "C"; "A and B"; "A and C"; "B and C"; and "A, B, and C."

The invention claimed is:

1. A healthcare information management system, comprising:

a structured database storing patient healthcare data in non-transient memory according to a unified schema that is the same for each patient whose healthcare data is stored in the structured database, the unified schema having a plurality of distinct data fields including a patient ID field, each data field being pre-defined by a data field definition having a plurality of distinct parameters; and a data processor configured to receive from at least one user interface an upload of unstructured healthcare information of a patient, the data processor being configured to, upon receipt of the unstructured healthcare information, automatically:

convert documents, text conversations, and audio information of the unstructured healthcare information that is not already in text form to text form, chunk the text from the converted documents, text conversations, and audio information, generate vector embeddings from video and image information of the unstructured healthcare information, generate a single data dump combining the chunked text and the vector embeddings, store the data dump in an index, identify relevant portions of the data dump to search for relevant healthcare data of the patient to extract and store in the structured database, provide a natural language instruction to a large language model (LLM) to search only the identified relevant portions of the data dump for the relevant healthcare data, wherein the natural language instruction is generated from a pre-defined LLM instruction template that is populated, for each distinct data field of the structured database, with the data field definition for that data field and the identified relevant portions of the data dump, and store the relevant data returned by the LLM in the pre-defined data fields of the structured database, wherein the relevant data is defined as data for which there is a pre-defined data field in the structured database, and unstructured information is defined as information in which at least a portion of the information is not organized according to a defined schema.

2. The system of claim 1, wherein the data processor is configured to identify the relevant portions of the data dump via retrieval-augmented generation (RAG).

3. The system of claim 1, wherein the data processor is configured to simultaneously receive the unstructured healthcare information in at least two different file formats, understand and parse the received unstructured healthcare information, and generate the single data dump from the understood and parsed unstructured healthcare information.

4. The system of claim 1, wherein the data processor is configured to generate vector embeddings based on the chunked text, and include the vector embeddings in the single data dump.

5. The system of claim 1, wherein the data processor is configured to provide a pre-defined natural language LLM graph generation instruction to the LLM to generate a graph from the chunked text and generate vector embeddings from the graph.

6. The system of claim 5, wherein the data processor is configured to identify the relevant portions of the data dump via graph-based retrieval augmented generation (GraphRAG).

7. The system of claim 1, wherein the data processor, in response to receiving an outcome request, provides the request to a large language model (LLM) to understand the request and retrieve pertinent data from the structured database, the requested outcome being generated based at least in part on the retrieved pertinent data, wherein pertinent data is defined as data in the structured database that is pertinent to the outcome request.

8. The system of claim 7, wherein the data processor is configured to input the structured database to the LLM to understand the request and retrieve the pertinent data.

9. The system of claim 7, wherein the data processor is configured to generate processed pertinent data by providing to the LLM a pre-defined LLM instruction, the retrieved pertinent data, and details of the outcome request, wherein the processed pertinent data includes at least one of: a summary of the pertinent data, an analysis of the pertinent data, or insights based on the pertinent data.

10. The system of claim 9, wherein the data processor is configured to generate a formatted output by providing to the LLM a pre-defined LLM outcome generation instruction, the retrieved pertinent data, the processed pertinent data, details of the outcome request, and a specified output format.

11. The system of claim 7, wherein the pertinent data includes data extracted from received healthcare information previously input into the system in multiple different file formats.

12. The system of claim 1, wherein the data processor is configured to identify potential new data fields to add to the structured database, by providing inputs to the LLM including:

an LLM data extraction instruction, a data dump generated by the data processor prior to extraction of the relevant data from the received healthcare information, and definitions of each data field of the structured database, wherein the data processor stores identified potential new data fields in a pool of potential new data fields and is configured to add one or suggest adding one or more fields of the potential new data fields in the pool to the structured database when said one or more fields of the potential new data fields reaches a threshold significance.

13. The system of claim 1, further comprising a data field customization interface by which a user can add new data fields, remove existing data fields, or modify existing data fields of the structured database.

14. The system of claim 1, wherein the structured database includes one or more data fields or metadata identifying one or more entities authorized to access at least one data field of the structured database, and wherein the data processor, in response to receiving an outcome request from a user, is configured to determine whether the user has authority to access the at least one data field before generating the outcome.

15. The system of claim 1, wherein the system is configured to use the unified schema as an organizational structure for the patient healthcare data and as an aid in processing the received unstructured healthcare information to identify the relevant data to store in the data fields of the structured database.

16. The system of claim 1, wherein the unified schema comprises an array of patient healthcare data.

17. The system of claim 1, wherein the structured database is a relational database that is searchable using structured query language.

18. The system of claim 1, wherein the data processor is configured to not extract healthcare data from the data dump when no relevant healthcare data is returned by the LLM in response to the natural language instruction.

* * * * *